(12) United States Patent
Hausheer et al.

(10) Patent No.: US 6,169,080 B1
(45) Date of Patent: *Jan. 2, 2001

(54) HIGHLY LIPOPHILIC CAMPTOTHECIN DERIVATIVES

(75) Inventors: Frederick H. Hausheer, Boerne; Kochat Haridas, San Antonio; P. Seetharamulu, San Antonio; Dasharatha G. Reddy, San Antonio; Shijie Yao, San Antonio; Pavankumar N.V. Petluru, San Antonio; Dhanabalan Murali, San Antonio, all of TX (US)

(73) Assignee: BioNumerik Pharmaceuticals, Inc., San Antonio, TX (US)

( * ) Notice: Under 35 U.S.C. 154(b), the term of this patent shall be extended for 0 days.

This patent is subject to a terminal disclaimer.

(21) Appl. No.: 09/022,310

(22) Filed: Feb. 11, 1998

Related U.S. Application Data

(60) Provisional application No. 60/037,995, filed on Feb. 13, 1997, and provisional application No. 60/037,148, filed on Feb. 14, 1997.

(51) Int. Cl.$^7$ ...................... A61K 31/475; A61K 31/695; C07D 491/22; A61P 35/00
(52) U.S. Cl. .............................. 514/63; 514/283; 546/14; 546/48
(58) Field of Search .......................... 546/14, 48; 514/63, 514/283

(56) References Cited

U.S. PATENT DOCUMENTS

| | | | |
|---|---|---|---|
| 4,399,282 | * 8/1983 | Miyasaka | 546/48 |
| 5,061,800 | * 10/1991 | Yaegashi | 546/48 |
| 5,391,745 | * 2/1995 | Danishefsky | 546/48 |
| 5,468,859 | * 11/1995 | Fortunak | 546/48 |
| 5,910,491 | * 6/1999 | Hausheer | 514/63 |

FOREIGN PATENT DOCUMENTS

2534601 * 2/1977 (DE) .

* cited by examiner

Primary Examiner—Evelyn Mei Huang
(74) Attorney, Agent, or Firm—Thomas J. Dodd

(57) ABSTRACT

This invention relates to novel derivatives of camptothecin, and will, particularly to derivatives having a substitution at the C-7 position, or at one of the C-9, C-10, C-11 or C-12 positions, or to disubstituted derivatives having a first substitution at C-7 and a second at one of C-9, C-10, C-11 or C-12. The invention also includes methods of using the compounds as Topoisomerase I inhibitors to treat patients with cancer. The invention also includes pharmaceutical formulations which consist of the novel compounds in solution or suspension with one or more pharmaceutical excipients or dilutes.

10 Claims, No Drawings

HIGHLY LIPOPHILIC CAMPTOTHECIN DERIVATIVES

This application claims the benefit of provisional applications No. 60/037,995, filed on Feb. 13, 1997 and 60/037,148, filed on Feb. 14, 1997.

FIELD OF THE INVENTION

This invention relates to novel derivatives of camptothecin, and will have special application to derivatives having substitutions at the C-7 position, and also at one of the C-9, C-10, C-11 or C-12 positions.

BACKGROUND OF THE INVENTION

Camptothecin (CPT) and certain of its derivatives are potent anti-cancer agents and have been the subject of intensive research since the discovery and isolation of camptothecin more than 30 years ago.

CPT was isolated in 1966 by Wall and Wani from *Camptotheca accuminata*, a Chinese yew. CPT was subsequently observed to have potent anti-cancer activity and was introduced into human clinical trials in the late 1970's. CPT lactone was noted to be very poorly water soluble (about 1 $\mu$g/mL), and in order for CPT to be administered in human clinical trials it was originally formulated with sodium hydroxide which increased the solubility of the drug. Sodium hydroxide formulation of camptothecin resulted in hydrolysis of the lactone E-ring of the camptothecin molecule, and formed the water soluble CPT carboxylate species. The sodium hydroxide formulation of CPT created a water soluble CPT species that permitted clinicians to administer larger doses of the drug to cancer patients undergoing Phase I and Phase II clinical trials.

Years later that it was learned that the carboxylate species of parenterally administered CPT had approximately one-tenth or less of the antitumor potency of the lactone form. Clinical trials with sodium hydroxide formulated CPT were disappointing due to significant systemic toxicity and the lack of substantive anti-tumor activity, and clinical studies of CPT were temporarily abandoned in the early 1980's.

Further clinical development of camptothecin derivatives was not pursued until the mid-1980's. At that time it was reported that CPT had a unique mechanism of action which involved the inhibition of DNA synthesis and DNA replication by interactions with the ubiquitous cellular enzyme Topoisomerase I (Topo I). This new information about the mechanism of action of camptothecin derivatives rekindled the interest in developing new Topo I inhibitors as anti-cancer drugs. Subsequently, several research groups began attempting to develop new camptothecin derivatives for cancer therapy. In general, it was observed that camptothecin and many of its derivatives exhibited very poor water solubility. This poor water solubility limited the clinical utility of the drug because prohibitively large volumes (e.g., 5 or more liters) of water had to be delivered to the patient in order to administer an effective dose of the drug. Because of the poor water solubility, a great deal of research effort was directed at generating water soluble CPT derivatives.

Some of the more well-known water soluble camptothecin derivatives include: 9-dimethylaminomethyl-10-hydroxy camptothecin (Topotecan), 7-[(4-methylpiperazino)methyl]-10,11-ethylenedioxy camptothecin, 7-[(4-methylpiperazino) methyl]-10,11-methylenedioxy camptothecin, and 7-ethyl-10-[4-(1-piperidino)-1-piperidino]carbonyloxy camptothecin (CPT-11).

Other substituted camptothecin derivatives with different solubility and pharmacologic properties have been synthesized as well; examples of these camptothecin derivatives include 9-amino camptothecin and 9-nitro camptothecin which are both are poorly soluble in aqueous and nonaqueous media and have been tested in humans.

Of this diverse group of substituted camptothecin derivatives undergoing human clinical development, CPT-11 is one of the most extensively studied in clinical trials in human patients with cancer. CPT-11 (Irinotecan/Camptosar®) was approved for human use by the FDA in June, 1996. It is noteworthy that CPT-11 is biologically inactive and requires activation by a putative carboxylesterase enzyme. The active species of CPT-11 is the depiperidenylated 10-hydroxy 7-ethyl camptothecin (claimed in Miyasaka et al. U.S. Pat. No. 4,473,692 (1984)), also known as SN38. SN38 is a toxic lipophilic metabolite which results from in vivo bioactivation of CPT-11 by a carboxylesterase enzyme. SN38 is very poorly soluble in water and has not been directly administered to human patients with cancer. Recently it has been reported in human patients that SN38 undergoes further metabolism to form an inactive glucuronide species. The glucuronide species also appears to be involved in producing human toxicity (diarrhea and leukopenia are the major dose-limiting toxicities) and substantial interpatient variability in drug levels of the free metabolite and its glucuronide. CPT-11 has been studied in human clinical trials in the United States, Europe and Japan and several patient deaths due to drug toxicity have been reported in association with the use of CPT-11.

In view of the very limited number of potentially active camptothecin derivatives in the poorly water soluble/highly lipid soluble category, there clearly remains a large unmet need to develop potent, poorly water soluble, highly lipophilic camptothecins which do not require metabolism to an active species and are less susceptible to metabolic inactivation and clinically important types of drug resistance in tumors.

SUMMARY OF THE INVENTION

The new compositions of matter disclosed and claimed in the present invention address these unmet needs and can, in addition to topical and parenteral routes of administration, be administered orally which is more convenient for many patients undergoing treatment for cancer.

The present invention overcomes the prior art limitations and has significant utility in patient safety, because these new compositions do not undergo A-ring or B-ring glucuronidation (and implicitly deglucuronidation) and they are not prodrugs which require metabolic activation. Also, because the compounds are lipophilic and can be directly administered in their active lactone form, it is submitted that they will have superior bioavailability relative to CPT-11, Topotecan, 9-amino camptothecin, 9-nitro camptothecin, 7-[(4-methylpiperazino)methyl]-10,11-ethylenedioxy camptothecin, 7-[(4-methylpiperazino)methyl]-10,11-methylenedioxy camptothecin, and other forms of the drug.

The instant invention is also aimed at overcoming other important limitations in bioavailability/pharmacokinetics and common tumor mediated drug resistance mechanisms (e.g., MDR, MRP, LRP) observed with the use of water soluble camptothecins or 9-amino or 9-nitro substituted camptothecins as anticancer agents.

The novel camptothecin derivatives claimed in the present invention represent a new class of antitumor compounds that do not require metabolic activation and exhibit potent antitumor activity against common types of human cancer including but not limited to cancers of the lung, breast, prostate, pancreas, head and neck, ovary and colon. The compounds described by the instant invention have also been shown effective against malignant melanoma neoplasms.

The compounds of this invention all possess Topoisomerase I inhibitory activity similar to that of other camptothecin derivatives but have significant structural modifications rationally designed for superior active site binding capability and tissue penetration. The compounds are designed to avoid untoward metabolism and drug resistance mechanisms which are common in mammalian tumors. Until now, lipophilic camptothecin derivatives with poor water solubility have not been pursued because of limitations in pharmaceutical formulations and methods of use. These novel camptothecin derivatives can be readily formulated in a pharmaceutically acceptable manner by dissolving the drug composition in an organic solvent, or in a mixture of organic solvents which have a high degree of physiologic safety. This allows for the direct administration of these new and non-obvious compounds to cancer patients.

The inventors have discovered several new derivatives of CPT, essentially an entirely new class of molecules which include substitutions at one or more of the a) C-7; and/or b) one of the C-9, C-10, C-11 or C-12 positions in the 20(S)-camptothecin molecule or 20(RS)-camptothecin mixture. These new compounds all possess the following characteristics:

1. Potent antitumor activity (nanomolar or subnanomolar activity in inhibiting the growth of human tumor cells in vitro);
2. Potent inhibition of human Topoisomerase I;
3. Lack of susceptibility to MDR/MRP/LRP drug resistance;
4. Lack the requirement for metabolic drug activation;
5. Do not undergo A-ring or B-ring glucuronidation;
6. Can be administered in the lactone species directly to patients for the purpose of treating a variety of cancers;
7. Low molecular weight (e.g., MW <600);
8. Highly soluble in organic pharmaceutical solvents or co-solvents (e.g., propylene glycol, PEG 300–400, dimethyl acetamide (DMA), dimethyl isosorbide (DMI), N-methyl pyrrolidinone (NMP)); and
9. Can be administered orally, in addition to parenterally and topically, to subjects with cancer.

This invention has, as its primary objective, the creation of new and useful lipophilic, poorly water soluble, substituted camptothecin derivatives suitable for nonaqueous oral and parenteral formulations, to be administered to patients with cancer. This invention also teaches new convergent and efficient chemical syntheses of these novel substituted camptothecin derivatives using commercially available and relatively inexpensive natural isolates of camptothecins. Accordingly, a number of new A-ring and B-ring modifications are taught in this invention.

The present invention teaches a novel process of homolytic acylation of camptothecin and camptothecin derivatives regiospecifically at the C-7 position based on a Minisci type reaction. A slight variation to the earlier stated methodology for C-7 alkylation permits the stabilization of the transient acyl radical that enables acylation of the parent scaffold in high yield. The present invention also describes novel processes to make certain key versatile synthons for extensive chemical transformations at the C-7 position, and/or at one of the C-9, C-10, C-11 or C-12 positions.

The novel compounds of this invention are of the following formula:

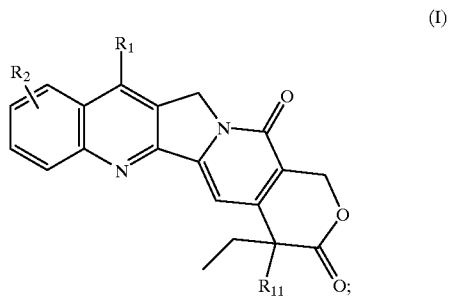

(I)

wherein $R_1$ is hydrogen; acyl, $C_2$–$C_8$ alkenyl, or $C_2$–$C_8$ alkynyl optionally substituted by one or more halogen atoms or $OR_4$ or lower alkyl for a corresponding hydrogen atom therein; oxo; aryl; arylalkyl; arylalkenyl; arylalkynyl; heterocycle; $SR_5$; —S(O)-lower alkyl; -lower alkyl-P(O)$R_6R_7$, or X—($C_0$–$C_6$ alkyl, $C_0$–$C_8$ alkenyl, or $C_0$–$C_8$ alkynyl)—$SiR_8R_9R_{10}$;

$R_2$ is hydrogen, halo, lower alkyl, amino or nitro, provided that $R_1$ and $R_2$ are not both hydrogen;

$R_4$ is hydrogen or lower alkyl;

$R_5$ is hydrogen or lower alkyl;

$R_6$ and $R_7$ are each individually hydrogen or lower alkyl;

$R_8$, $R_9$ and $R_{10}$ are each individually hydrogen or lower alkyl;

$R_{11}$ is hydrogen, hydroxy or acetoxy; and

X is sulfur or X is absent; or a pharmaceutically acceptable salt thereof.

It is therefore a principal object of this invention to provide for new, useful and non-obvious lipophilic and poorly water soluble derivatives of camptothecin, in particular, substituted analogs having either a substitution at the C-7 position, or a substitution at one of the C-9, C-10, C-11 or C-12 positions of the molecule, or a disubstituted camptothecin having a first substitution at C-7, and a second substitution at one of C-9, C-10, C-11 or C-12. Most preferably, the compounds of this invention will be substituted at the C-9 or C-10, or disubstituted at C-9 or C-10, and C-7.

It is another object of the present invention to provide a fascile and efficient synthetic methodology for the preparation of a new class of substituted camptothecins.

Another object of the present invention includes the manufacture and utilization of the versatile 7-triflyloxy camptothecin as a key intermediate for the preparation of widely varied multi-substituted camptothecins.

Another object of this invention is to provide a method of treating mammalian cancers and leukemias by administering an antineoplastic or antileukemic dose of the novel CPT derivatives to a patient diagnosed with cancer or leukemia.

Another object of this invention is to provide for pharmaceutical formulations of the novel CPT derivatives, which may be administered to patients parenterally, orally or topically.

Other objects of this invention will become apparent upon a reading of the following specification.

DESCRIPTION OF THE PREFERRED EMBODIMENTS

Definitions

"Scaffold" means the fixed part of the molecule of the general formula given.

"Fragments" are the variable moieties of the molecule, designated in the formula by variable symbols, such as $R_x$ or the like. Fragments may include one or more of the following moieties:

"$C_x$–$C_y$" alkyl means a straight-chain or branched-chain hydrocarbon containing as few as x and as many as y carbon atoms. Examples include "$C_1$–$C_6$ alkyl" (also referred to as "lower alkyl"), which includes a straight or branched chain hydrocarbon with no more than 6 total carbon atoms.

"$C_x$–$C_y$ alkenyl" or "$C_x$–$C_y$ alkynyl" means a straight or branched chain hydrocarbon with at least one double bond (alkenyl) or triple bond (alkynyl) between two of the carbon atoms.

"Halogen" or "Halo" means chloro, fluoro, bromo or iodo.

"Acyl" means —C(O)—X, where X is hydrogen, lower alkyl, aryl, lower alkenyl or lower alkynyl.

"Aryl" means an aromatic ring compound of one or more rings comprised entirely of carbon atoms.

"Arylalkyl" means an aromatic ring as defined above, bonded to the scaffold through an alkyl moiety (the attachment chain).

"Arylalkenyl" and "Arylalkynyl" both mean the same as "Arylalkyl", but including one or more double or triple bonds in the attachment chain.

"Heterocycle" means a cyclic moiety of one or more rings, fused or unfused, wherein at least one atom of one of the rings is a non-carbon atom. Preferred heteroatoms include oxygen, nitrogen, sulfur and phosphorous, or any combination of two or more of those atoms.

"Alkoxycarbonyl" means an alkoxy moiety bonded to the scaffold through a carbonyl.

"Acyloxy" means an acyl moiety bonded to the scaffold through an oxygen atom.

Examples of the above moieties are as follows:

$C_1$–$C_6$ alkyl includes methyl, ethyl, propyl, isopropyl, butyl, isobutyl, sec-butyl, tert-butyl, pentyl, hexyl, amyl and the like;

$C_2$–$C_8$ alkenyl or alkynyl includes vinyl, propenyl, butenyl, acetylenyl, propynyl, and other like moieties with double and triple bonds;

Acyl includes formyl, acetyl, propionyl and others;

Aryl includes phenyl and naphthyl, as well as substituted variants wherein one of the hydrogen atoms bonded to the ring atom is substituted by a halogen atom, an alkyl group, or another of the above-listed moieties;

Arylalkyl includes benzyl, phenethyl, and the like;

Arylalkenyl and arylalkynyl includes phenyl vinyl, phenylpropenyl, phenylacetylenyl, phenylpropynyl and the like; and Heterocycle includes furanyl, pyranyl, thionyl, pyrrolyl, pyrrolidinyl, prolinyl, pyridinyl, pyrazolyl; imidazolyl, triazolyl, tetrazolyl, oxathiazolyl, dithiolyl, oxazolyl, isoxazolyl, oxadiazolyl, pyridazinyl, pyrimidinyl, pyrazinyl, piperazinyl, oxazinyl, thiazolyl, and the like, as well as fused ring heterocycles such as benzopyranyl, benzofuranyl, indolyl, phthalyl, quinolinyl, pteridinyl, and the like.

Alkoxycarbonyl includes methoxycarbonyl, ethoxycarbonyl, isopropoxycarbonyl, and the like.

Acyloxy includes formyloxy, acetoxy, propionyloxy, and the like.

The camptothecin derivatives of the present invention have the following general formula:

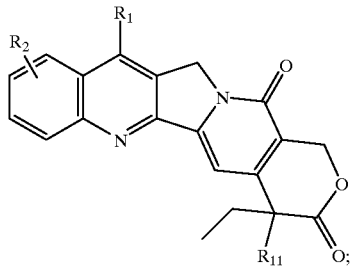

(I)

wherein $R_1$ is hydrogen; acyl, $C_2$–$C_8$ alkenyl, or $C_2$–$C_8$ alkynyl optionally substituted by one or more halogen atoms or $OR_4$ or lower alkyl for a corresponding hydrogen atom therein; oxo; aryl; arylalkyl; arylalkenyl; arylalkynyl; heterocycle; $SR_5$; —S(O)-lower alkyl; -lower alkyl-P(O)$R_6R_7$, or X—($C_0$–$C_6$ alkyl, $C_0$–$C_8$ alkenyl, or $C_0$–$C_8$ alkynyl)-Si$R_8R_9R_{10}$;

$R_2$ is hydrogen, halo, lower alkyl, amino or nitro, provided that $R_1$ and $R_2$ are not both hydrogen;.

$R_4$ is hydrogen or lower alkyl;

$R_5$ is hydrogen or lower alkyl;

$R_6$ and $R_7$ are each individually hydrogen or lower alkyl;

$R_6$, $R_9$ and $R_{10}$ are each individually hydrogen or lower alkyl;

$R_{11}$ is hydrogen, hydroxy or acetoxy; and

X is sulfur or X is absent; or a pharmaceutically acceptable salt thereof.

The compounds of Formula I are synthesized preferably according to the following procedures.

Alkylation of protonated camptothecin

The homolytic alkylation of camptothecin is generalized for a variety of alkyl substitutions at the C-7 position. While designing these processes for scale-up synthesis, factors such as simplicity, economy and availability of certain reagents, overall yield and selectivity have been carefully considered. The Minisci type alkylation (Minisci, F., 1973) is also optimized for various phenolic camptothecins without prior protection to the phenolic moiety. Minisci type alkylations of heteroaromatic bases have several advantages. Polar effects related to the nucleophilic character of the carbon-centered radicals and the electron deficiency of the protonated heterocyclic bases play a significant role in the synthetic yield of these reactions. Reactivity and positional and substrate selectivity are two of the major merits (Vorbruggen, H., 1988). The rearomatization of the radical adduct is very selective and quick rapid due to strongly nucleophilic radicals of the pyridinyl type. Reactions of this category are an Iron (II) salt mediated exothermic process that affords selective substitutions at α or γ positions of the heterocyclic ring. In the present invention, we have taken advantage of these factors to selectively introduce alkyl substitutions at the C-7 position of camptothecin skeleton such as certain novel lower alkyl groups, trifluoroethyl, polyfluoroethyl and monofluoro ethyl groups.

C-7 Acylation of protonated camptothecin:

Acylation of the heteroaromatic bases such as camptothecins are of great interest due to the fact that electrophilic aromatic substitutions are generally ineffective with these types of heterocyclic systems. Further, the high reactivity and selectivity of the C-7 position of camptothecin due to increased nucleophilicity under acidic conditions would provide the desired products with minimal unwanted by-products. The respective acyl radicals can easily be obtained from the corresponding aldehydes in the presence of excess trifluoro acetic acid at low temperature. Minisci type alkylation procedures were found extremely effective with various camptothecin derivatives. However, Minisci-type acylations of CPT have not to date been reported. These types of homolytic substitutions are of significant value as an alternate tool for heterocyclic systems where classical Friedel-Crafts reactions can not be effectively performed. The present invention teaches such novel acylation reactions on the quinoline bearing CPT skeleton.

In principle, the more stable the carbonium ion is the more nucleophilic will be the corresponding radical. Therefore, almost all the electrophilic species that are useful in the Friedel-Craft reaction can be utilized, as the corresponding radicals, for the selective substitution of the heteroaromatic bases. This opens a wide variety of organic compounds as radical sources for C-7 substitution of camptothecin. Those types of compounds include: alkanes, alkenes, alkylbenzenes, alkyl halides, alcohols, ethers, aldehydes, ketones, carboxylic acids, amines, amides, oxaziridines, N-chloramines etc. The inventors submit that the major determinants of the reaction conditions that lead to either the desired alkylated product or acylated product are largely controlled by the type of acid present in excess and the free radical initiator.

C-7 Halogenation:

Chlorination and bromination at the C-7 position of camptothecin are best done on an electron deficient nitrogen bearing camptothecin skeleton. It is very evident from the literature that the oxide function at $N^1$ position of a quinoline moiety could generate substantial nucleophilicity to $\alpha$ and $\gamma$ positions of the heterocylic base. Such effects would be enhanced further upon a protonation event on the N-oxide. In the case of camptothecin skeleton, an absolute $\gamma$ selectivity is envisioned as the a positions are already blocked. The inventors' observed that such nucleophilic halogenation proceeds smoothly and selectively on 20-acetoxy- camptothecin 1- oxide in presence of excess trihalophosphine oxide at 40° C. The camptothecin derivatives thus prepared are subsequently utilized as synthons for cross-coupling reactions as stated below.

Stille type coupling at the C-7 position:

Stille's procedure (J, K. Stille, 1986; J, K. Stille 1987) provides one of the most useful methods to construct carbon-carbon single bonds. The reaction is catalyzed by organometallic reagents derived from group IA metals via coupling of organic electrophiles and organostannanes in presence of lithium halide. Similar cross coupling where boronic acids or esters are employed in place of organostannanes are called Suzuki cross-coupling Reaction (George B. S., 1994). Excess stoichiometric amounts of lithium chloride are essential for the completion of the reaction as lithium chloride is consumed for the formation of tributyltin chloride and lithium triflate. A variety of organic electrophiles are used in the cross-coupling reaction of which bromides, iodides and triflates are extensively studied (Kurt Ritter, 1993). The rate of the reaction can be modulated readily based on the composition and concentration of the organic electrophile. A better understanding of the mechanistic aspects of the rate limiting transmetallation process led to the recent developments involve the use of cocatalytic Cu(I) and Pd(0) species in this coupling reaction. The role of the Cu(I) species has been envisioned (Liebeskind, 1990) in Sn/Cu transmetallation. The resulting organocopper species would then transmetallate onto Pd(II) at a higher rate than the stannane itself. This is currently known as the "copper effect." The scope of the reaction is extremely wider than this application. A large number of structurally varied organic groups including vinyl, alkyl, allyl, aryl, acetylenic, amino, amido and [(trimethylsilyl)methyl] moieties on tin could easily be transferred onto aryl and heteroaryl skeletons displacing the vinyl triflate or unsaturated halides in high yields. However, the conventional Stille reaction conditions are unacceptable for some of our novel entities. Further, modifications were sought out in this direction that resulted in making the palladium catalyzed cross-coupling highly conceivable to incorporate such functionalities in extremely mild conditions as well as in high yields. In all these coupling reactions, tris(dibenzylideneacetonyl)bis palladium(0) served as the catalyst while tri(2-furyl) phosphine exhibited its noticeable role in enhancing the rate of activation of the ligand properties even at room temperature.

Suzuki Cross-Coupling Reaction:

The Stille coupling and the Suzuki coupling are very similar in many respects at a fundamental level, however, in terms of scalability for large scale production of the new compositions the Suzuki coupling has certain advantages. The necessary use of tin in stoichiometric amounts in the Stille reaction makes the Suzuki coupling more attractive. However, no generally applicable set of reaction conditions has yet been found to affect this reaction. At the same time, Suzuki coupling is an extremely convergent approach for the incorporation of cyclopropyl, phenyl and certain other polyfluoroalkyl functionalities into a camptothecin scaffold. Recent reports by Wright and co-workers (Wright, S. W., 1994) simplified the reaction conditions by employing fluoride ion instead of incompatible bases to generate boronate anion. However, boronate anion may be crucial in the reaction medium to effect boron to palladium transmetallation. The recent report unambiguously suggested the capability of fluoride ions to exhibit significant affinity for boron and considerable stability of fluoborate ions. Additionally, the report also has addressed the favoring weak basicity and poor nucleophilicity of fluoride ions and the weakness of the palladium-fluorine bond in Suzuki coupling reactions.

The following Schemes illustrate the general processes used to produce novel camptothecin derivatives of this invention, and in no way are to be considered limiting of the invention.

Scheme 1

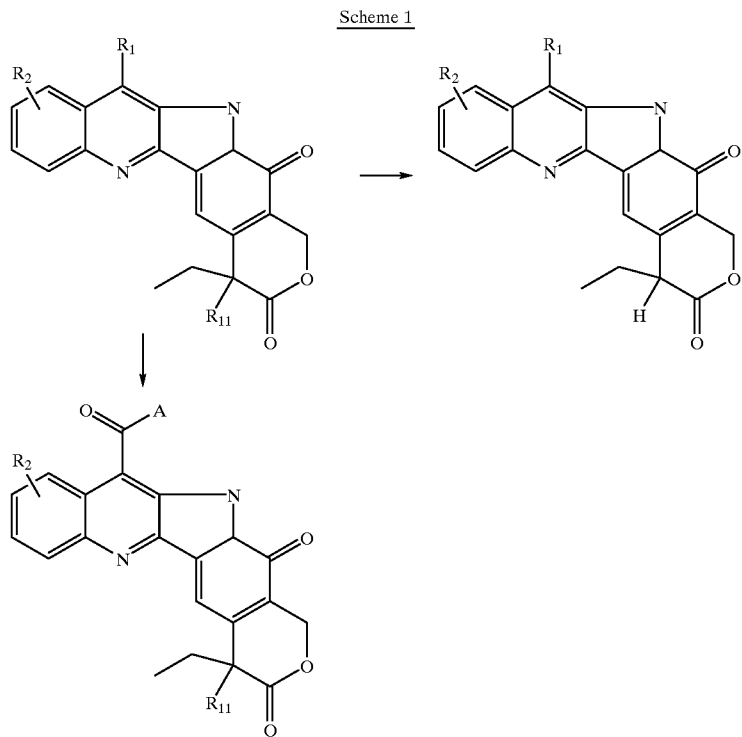

Scheme I illustr the preparation of the C-7 acyl derivatives of this invention, and also the preparation of the 20-dehydroxy derivative of CPT.

The selective acylation at the C-7 position on the B-ring is achieved by the procedures outlined above. In the above scheme, "A" represents an alkyl chain of 1–6 Carbon atoms, most preferably 1–2 Carbon atoms, to form 7-Acetyl CPT or 7-Propionyl CPT, and $R_{11}$ is hydroxy.

Conversion of the 20-hydroxy moiety to a hydrogen atom is achieved by a selective 20-position deoxygenation. Typical reagents are bases, such as Lawsson's Reagent, or similar compounds.

Scheme 2

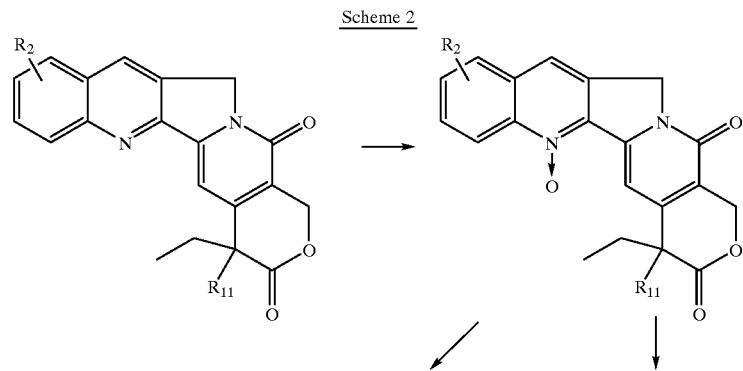

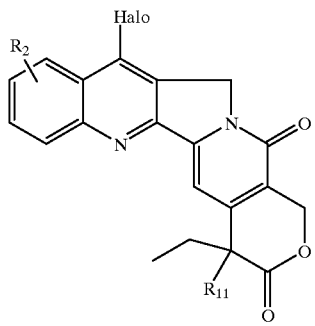
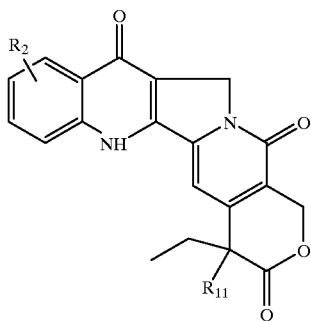

Scheme II illustrates the preparation of 7-halo CPT derivatives, and also the preparation of the key intermediate 7-keto CPT. The first step in the synthesis of either of these compounds is the conversion of CPT to camptothecin-1-oxide. In Scheme II, $R_{11}$ is typically a protected hydroxy moiety, most preferably an acetoxy moiety, which is deprotected back to a hydroxy moiety after the 7-position moieties have been added. Typical deprotection of the 20-acetoxy moiety and conversion to 20-hydroxy is accomplished by use of alkali metal salts and aqueous alcohols, most preferably potassium carbonate and methanol.

The halogenation at C-7 is also achieved by the general procedures described above. Conversion and regioselectivity of CPT-1-oxide to 7-keto CPT is also described above, with the most preferred procedures outlined in Example 3 below. 7-Keto CPT is used extensively as a key intermediate in many of the selective schemes for producing the 7-substituted CPT derivatives of this invention.

Scheme 3

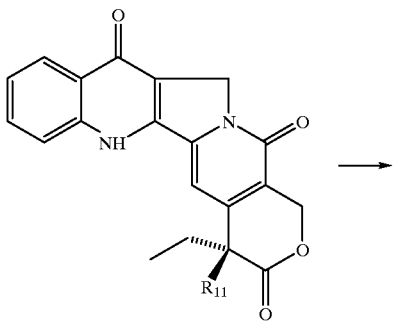

-continued

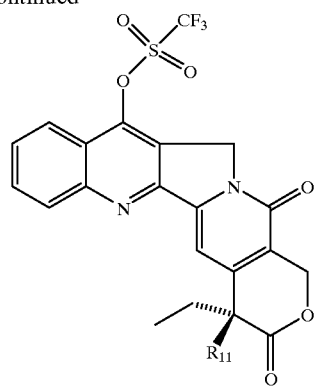

Schemes III and IV detail the synthetic procedures for making the novel CPT derivatives which form the subject matter of this invention.

Scheme III illustrates the synthesis of the 7-trifluoromethanesulfonyloxy (triflyloxy) intermediate which is key to the substitution of various 7-position moieties which form the subject matter of this invention.

As shown, 7-keto CPT is converted into the triflate intermediate by reacting with a sulfonate ester and an alkali metal salt, or with triflic anhydride. The resulting 7-triflate intermediate possesses excellent properties for substitution reactions to be performed on the molecule, allowing for diverse moieties to be attached to the CPT scaffold.

Scheme 4

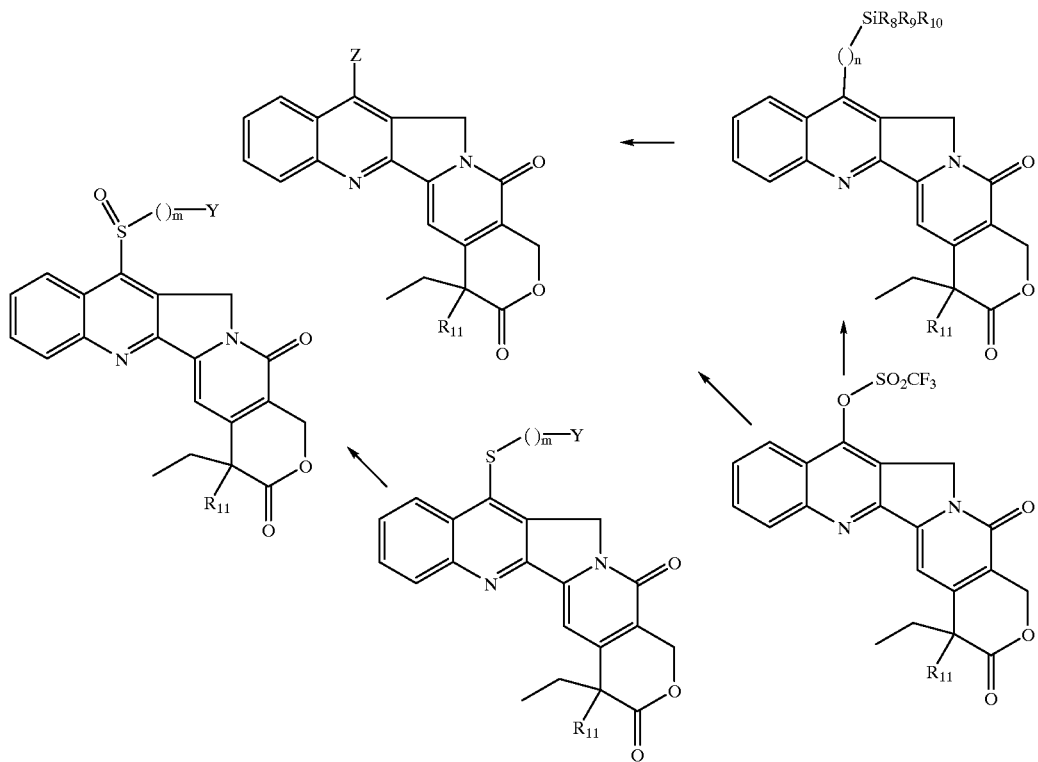

Scheme IV illustrates the synthesis of the novel C7-substituted CPT derivatives of this invention. The key intermediate, 7-trifluoromethanesulfonyl CPT, is converted into one of the novel compound of this invention by following the general methods outlined in the specification, supra.

The two general moieties which are incorporated directly by displacing the triflyloxy moiety are the silyl moieties and the thioether moieties shown in scheme IV. As stated above, the silyl moieties are formed through a modified Stille coupling, through the use of a palladium mediated tributyltin-alkylsilane substitution. The $(\ )_{n-}$, refers to an alkyl (or alkenyl or alkynyl) group, where n stands for the number of carbon atoms, preferably 0 to 6, most preferably 0 to 3. When n is 0, the preferred synthesis utilizes an organolithium mediated displacement using hexamethyl disilane as the preferred reagent.

The silyl moieties may be converted into 7-alkenyl or 7-alkynyl moieties (designated by the letter "Z"), by reacting with an alkali metal salt, which both removes the silyl moiety and also serves to convert the 20-acetoxy moiety to the hydroxy moiety. 7-alkenyl and 7-alkynyl substituted CPT derivatives may also be prepared directly from the 7-triflate by the modified Stille coupling as described above.

7-thioethers are prepared by reacting the 7-triflate with the appropriate alkyl sulfide under basic conditions. In the scheme shown $(\ )_{m-}$ stands for an alkyl (or alkenyl or alkynyl) group and m is 0 to 6, preferably 1 to 3. Y indicates that a silyl moiety may be appended to the terminal end of the reagent, and will be transferred to the resulting compound. An example of such a thioether reagent is 2-trimethylsilyl ethyl-1-mercaptan, which would form 7-(β-trimethylsilyl) ethylthio CPT.

7-thioethers may be converted into the 7-sulfoxy derivatives by reacting with a per-acid, such as perbenzoic acid, most preferably m-chloroperbenzoic acid. Other derivatives may be prepared by utilizing the syntheses described above, in conjunction with the specific examples listed below.

Scheme 5

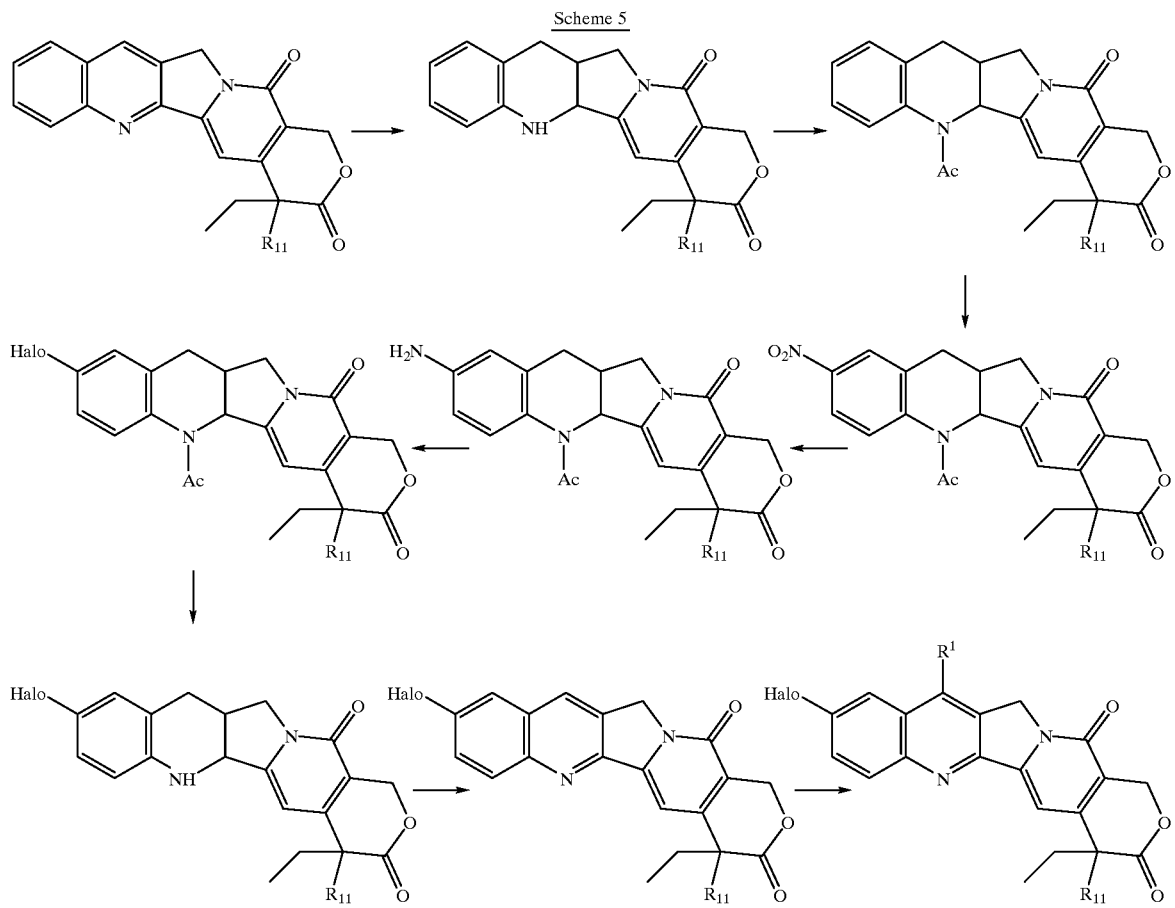

Scheme V illustrates the synthetic process for producing 10-substituted compounds of this invention, and also the general process for producing 7, 10 di-substituted derivatives of CPT. As shown, CPT is modified from its natural form to produce the 10-fluoro CPT derivative, and by extension, 7,10 di-substituted derivatives, as described and claimed in this invention.

In the preferred process, CPT is first hydrogenated to allow acylation of the N-1 nitrogen by reaction with an acylating agent, preferably an acid chloride, and most preferably, acetyl chloride to form the intermediate N-acetyl CPT. This intermediate is then subjected to a nitration reaction. The protected nitrogen acts as an amino moiety and selective addition of the nitro- group at the C-10 position (para) occurs. Manipulation of the reaction conditions and the base structure of the CPT intermediate determines where the nitro- group will attach to the scaffold. The positioning will be addressed in future applications by these applicants.

After nitration, the 10-nitro hydrogenated CPT is subjected to hydrogenolysis to convert the 10-nitro moiety to the more reactive 10-amino species. This conversion is preferably accomplished by bubbling hydrogen gas through a solution of the 10-nitro CPT in the presence of a catalyst. In the most preferred embodiment shown, hydrogen gas is bubbled through a polar solution of methanol and the 10-nitro intermediate in the presence of platinum oxide.

The 10-amino hydrogenated CPT is then halogenated (the 10-fluoro species is shown as the preferred species, but these procedures may also be used to synthesize other 10-halo CPT compounds). A halogenating agent, such as a boron trifluoride derived fluorinating reagent, is employed to effect halogenation. The most preferred agent is boron trifluoride diethyl etherate in an organic solvent, such as chloroform. To complete the reaction, the solution is refluxed in a nonpolar solvent, such as toluene.

As shown, the 10-halo hydrogenated CPT is then converted back to its dehydrogenated form by first deprotecting the N-1 moiety to remove the acetyl group, and then dehydrogenating the B-ring in a common manner. Preferably, a strong acid is employed to effect deprotection, and then a proton acceptor is employed to remove the extra hydrogens and restore the B-ring to its naturally unsaturated form. Most preferably, deprotection is effected with a mineral acid, such as sulfuric acid, and dehydrogenation is effected by an organic base, such as 2,3-dichloro-5,6-dihydro-1,4-benzoquinone (DDQ).

The 10-fluoro CPT may be converted to the 7,10 disubstituted species as shown. The 10-fluoro CPT is treated with an aldehyde to effect selective addition at the C-7 position according to the Minisci conditions described above. As shown in the most preferred scheme above, a trimethylsilyl alkyl moiety is added by reacting the 10-fluoro CPT intermediate with a trimethylsilyl (TMS) aldehyde to form a one carbon less TMS alkyl chain. In the most preferred compound described in the specific examples below, 3-trimethylsilyl propanal is the reagent used to produce the most preferred final compound, 10-fluoro-7-($\beta$-trimethylsilyl) ethyl camptothecin.

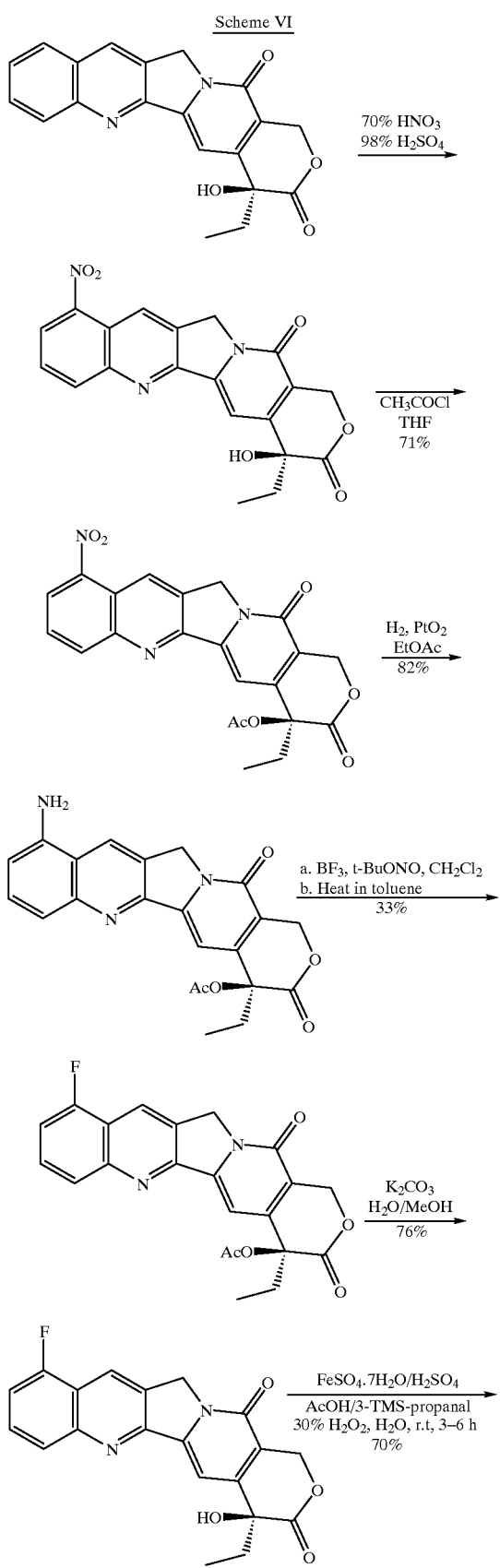

Scheme VI illustrates one general process for preparing 9-halo and 9,7-disubstituted derivatives of CPT. As shown, natural CPT is subjected to nitration, as by reaction with concentrated nitric acid. The addition of the nitro moiety to natural CPT selectively takes place at the 9-position, as shown.

Protection of the 20-hydroxy moiety, hydrogenation of the 9-nitro, conversion to 9-halo, deprotection, and the addition at the 7-position is effected similarly to the scheme shown above as Scheme V, with the exception that no operations are performed to selectively hydrogenate the B-ring, which is necessary in Scheme V to effect addition at the 10-position. Exact conditions of the most preferred synthesis are outlined in the specific examples below.

The schemes above have been set forth as general examples to assist those skilled in the art in the understanding of the present invention and in the synthesis of these novel and non-obvious compounds. The schemes are in no way intended as limiting of the invention, nor should they be construed as such.

The following specific examples illustrate selected modes for carrying out the invention and, like the schemes, are not to be construed as limiting the specification or the claims in any way.

EXAMPLE 1

7-Acetyl Camptothecin

Camptothecin (5 g, 14.36 mmol) was dissolved in trifluoroacetic acid/acetic acetic acid (60 mL; ratio, 1:1) and deionized water added (15 mL) along with freshly distilled acetaldehyde (20 mL; excess) followed by dropwise addition of concentrated sulfuric acid (5 mL) at 0° C. using an ice bath over a period of 15 minutes. To the above stirred reaction medium is then introduced a 70% aqueous solution of t-butylhydroperoxide (3 ml) followed by iron sulfate heptahydrate (7.8 g, 28 mmol) in 1 mL water. The reaction mixture was then stirred at 0° C. to 25° C. for an additional 24 hours. The reaction mixture was then diluted with water and extracted with diethyl ether (500 mL×1), chloroform (250 mL×1) and then n-butanol (250 mL ×4). The organic portions were extracted out using diethyl ether and chloroform and discarded as fractions lacking desired product, while the n-butanol portion was concentrated to dryness at 40° C. and the crude product was recrystallized from a 90% chloroform/methanol mixture to furnish 4.2 g of the title compound (75% yield).

$^1$H NMR (300 MHz; d6-DMSO): 0.87 δ (3 H, t, J=7 Hz); 1.86 δ (2 H, q, J=5 Hz); 2.78 δ (3 H, s); 5.29 δ (2 H, m); 5.38

δ (2 H, m); 6.51 δ (1 H, bs, OH); 7.35 δ(2 H, s); 7.78 δ (1 H, t, J=13.5 Hz); 7.92 δ (1 H, t, J=7.64 Hz); 8.13 δ (1 H, d, J=8.35 Hz); 8.23 d (1 H,d, J=8.38 Hz)
$^{13}$C NMR: δ 7.84, 30.41, 31.7, 50.27, 65.35, 73.21, 97.42, 119.78, 123.26, 124.86, 126.12, 131.4, 138.5, 143.87, 143.25, 145.31, 149.34, 150.05, 156.63, 157.68, 172.46, 205.05
FAB-MS: 391 (M+1)

EXAMPLE 2

7-Propionyl Camptothecin

Camptothecin (1 g, 2.8 mmol) was dissolved in trifluoroacetic acid/acetic acetic acid (6 mL; ratio, 1:1) and deionized water (3 mL) and freshly distilled propionaldehyde (3.0 mL; excess) were added, followed by dropwise addition of concentrated sulfuric acid (1 mL) at 0° C. using an ice bath over a 15 minute period. To the above stirred reaction medium was then introduced a 70% aqueous solution of t-butylhydroperoxide (3 mL) followed by iron sulfate heptahydrate (1.56 g, 5.6 mmol) in 1 ml water. The reaction mixture was then stirred at 0° C. to 25° C. for an additional 24 hours. The reaction mixture was then diluted with water and extracted with diethyl ether (100 mL×1), chloroform (50 mL×1) and then n-butanol (100 mL×4). The organic portions were extracted out using diethyl ether and chloroform, and were discarded as fractions lacking desired product, while the n-butanol portion was concentrated to dryness at 40° C. The crude product was recrystallized from a 90% chloroform/methanol mixture to furnish 0.86 g of the title compound (74% yield).
$^3$H NMR (300 MHz; d6-DMSO): 0.87 d (3 H, t, J=7 Hz); 1.26 δ (3 H, t, J=6.8 Hz); 1.84 d (2 H, q, J=5 Hz); 3.15 d (2 H, q, J=5.1 Hz); 5.29 δ (2 H, m); 5.38 δ(2 H, m); 6.51 δ (1 H, bs); 7.35 δ (2 H, s); 7.72 δ (1 H, t, J=13.5 Hz); 7.90 δ(1 H, t, J=7.64 Hz); 7.98 δ (1 H, d, J=8.35 Hz); 8.20 δ (1 H,d, J=8.38 Hz)
$^{13}$C NMR: δ 7.54, 7.74, 30.31, 36.7, 49.81, 65.21, 72.33, 96.88, 119.48, 123.12, 125.69, 130.63, 131.72, 140.97, 143.14, 143.25, 145.31, 149.97, 156.55, 157.68, 172.36, 204.91
FAB-MS: 405 (M+1)

EXAMPLE 3

7-Keto camptothecin (Camptothecinone)

Camptothecin 1-oxide (1 g, 2.7 mmol) was dissolved in trifluoroacetic acid (2 mL), anhydrous methylene chloride (15 ml) and added trifluoroacetic anhydride (16 mL). The reaction mixture was then refluxed under a positive pressure of argon for 48 hours. The reaction mixture was then cooled to room temperature and diluted with water (15 mL) and stirred for 6 hours. The product was then precipitated out by pouring the reaction mixture into crushed ice. The precipitated product was then filtered, washed with excess water, once with diethyl ether and dried under vacuum to obtain 687 mg of the desired product (66% yield).
$^1$H NMR (300 MHz; d6-DMSO): 0.87 δ (3 H, t, J=7 Hz); 1.96 δ (2 H, q, J=5 Hz); 2.78 δ (3 H, s); 5.86 δ (2 H, m); 5.40 δ (2 H, m); 6.81 δ (1 H, bs); 7.38 δ (1 H, t, J=13.5 Hz); 7.47 δ (2 H, s); 7.71 δ (1 H, t, J=7.64 Hz); 7.73 δ (1 H, d, J=8.35 Hz); 8.14 δ (1 H,d, J=8.38 Hz)
$^{13}$C NMR: δ 6.89, 29.55, 49.6, 66.123, 79.90, 94.78, 105.12, 118.48, 123.31, 124.26, 124.95, 132.06, 141.69, 143.55, 155.35, 164.88, 200.432
FAB-MS: 461 (M+1 for the triflic acid salt)

EXAMPLE 4

20-acetoxy-7-Trifluoromethanesulfonyloxy-camptothecin

20-Acetoxy camptothecinone (220 mg, 0.54 mmol) was dissolved in anhydrous pyridine (4 mL) and anhydrous methylene chloride (10 mL). The above solution was stirred well while lowering the temperature to −10° C. using an ice bath. To it was then slowly introduced triflic anhydride (0.5 ml, 1.05 mol) and the reaction continued to completion. The reaction mixture was then diluted with methylene chloride (20 mL), washed with water and the organic portion was concentrated to dryness. The product thus obtained upon analysis was found substantially pure for the subsequent step.
$^1$H NMR (300 MHz; CDCl$_3$): 0.87 δ (3 H, t, J=5.4 Hz); 2.12 δ (2 H, q, J=7.2 Hz); 2.21 δ (3 H, s); 5.42 δ(2 H, ABq, J$^1$=17.5 Hz; J$^2$=6.1 Hz); 5.49 δ (2 H, q, J=2.5 Hz); 7.14 δ (1 H, s); 7.97 δ (1 H, t, J=7.2 Hz); 8.05 δ (1 H, t, J=7.9 Hz); 8.12 δ (1 H, d, J=8.4 Hz); 8.35 δ (1 H, d, J=6.2 Hz)
FAB-MS: 540 (M+1)

EXAMPLE 5

20-Acetoxy-7-chloro camptothecin

20-Acetoxy camptothecin-1-oxide (800 mg, 1.96 mmol) was taken up as a suspension in phosphorus oxychloride (10 mL) and stirred at 40° C. for 48 hours under a positive blanket of inert gas. The reaction mixture was then diluted with methylene chloride (25 mL) and cooled to 0° C. using an ice bath. The reaction mixture was then diluted with water (50 mL) and stirred for 3 hours. The organic portion was then extracted out using methylene chloride (50 mL×5), concentrated and flashed through a bed of silica gel using chloroform to obtain the desired product (642 mg; 77.1% yield).
$^1$H NMR (300 MHz; CDCl$_3$): 0.90 δ (3 H, t, J=5.4 Hz); 2.12 δ (2 H, q, J=7.2 Hz); 2.21 δ (3 H, s); 5.42 δ (2 H, ABq, J$^1$=17.5 Hz; J$^2$=6.1 Hz); 5.49 δ (2 H, q, J=2.5 Hz); 7.07 δ (1 H, s); 7.87 δ (1 H, t, J=7.2 Hz); 7.95 δ (1 H, t, J=7.9 Hz); 8.21 δ (1 H, d, J=8.4 Hz); 8.27 δ (1 H, d, J=6.2 Hz)
FAB-MS: 425.1 (M+1 )

EXAMPLE 6

7-Chloro camptothecin

20-Acetoxy-7-chloro camptothecin (100 mg, 0.23 mmol) was dissolved in reagent grade methanol (20 mL) and added aqueous potassium carbonate (20 mg in 5 mL water) and stirred for 1 hour at room temperature. The resulting reaction mixture was concentrated to 5 mL under vacuum and diluted with water (20 mL). The precipitated product was then filtered, dried and analyzed to the desired product (60 mg; 67%).
$^1$H NMR (300 MHz; CDCl$_3$): 0.87 δ (3 H, t, J=5.4 Hz); 1.85 δ (2H, q, J=7.2 Hz); 3.6 δ (1 H, s); 5.31 δ (2 H, s); 5.43 δ (2 H, s); 7.07 δ (1 H, s); 7.87 δ (1 H, t, J=7.2 Hz); 7.95 δ (1 H, t, J=7.9 Hz); 8.21 δ (1 H, d, J=8.4 Hz); 8.27 δ (1 H, d, J=6.2 Hz)
$^{13}$C NMR: δ 7.54, 30.31, 49.81, 65.21, 72.33, 96.88, 119.48, 123.12, 125.69, 126.96, 130.63, 131.72, 140.97, 143.14, 143.25, 145.31, 149.97, 156.55, 157.68, 172.36
FAB-MS: 383.1 (M+1)

EXAMPLE 7

20 Acetoxy-7-vinyl-camptothecin

The 20-acetoxy-7-triflate (100 mg, 0.1855 mmol) was dissolved anhydrous and degassed anhydrous dimethylformamide (5 mL) and added zinc chloride (50.5 mg, 0.371 mmol). To it was then added tris(dibenzylideneacetonyl)bis palladium(0) (17 mg, 0.371 mmol) followed by tri(2-furyl)

phosphine (20 mg, 0.074 mmol). The resulting solution was stirred for approximately 30 minutes at room temperature. To it was added vinyl tributyltin (60 mL, 0.223 mmol). The reaction mixture was then stirred at room temperature for 48 hours. The resulting dark brown colored reaction mixture was then diluted with methylene chloride (25 mL), filtered, and washed with water (15 mL). The crude product obtained after concentration was then flashed through a columnar bed of florisil, the fractions pooled, concentrated, dried under vacuum and analyzed.

$^1$H NMR (300 MHz; CDCl$_3$): 0.87 δ (3 H, t, J=5.4 Hz); 1.85 δ (2 H, q, J=7.2 Hz); 2.31 δ (3 H, s); 3.6 δ (1 H, s); 5.42 δ (2 H, ABq, J$^1$=17.5 Hz; J$^2$=6.1 Hz); 5.61 δ (2 H, s); 6.15 δ (2 H, dd, J=12.8 Hz); 6.4 δ (1 H, d, J=2.5 Hz); 7.07 δ (1 H, s); 7.87 δ (1 H, t, J=7.2 Hz); 7.95 δ (1 H, t, J=7.9 Hz); 8.21 δ (1 H, d, J=8.4 Hz); 8.27 δ (1 H, d, J=6.2 Hz)

EXAMPLE 8

7-Vinyl camptothecin

20-Acetoxy-7-vinyl camptothecin (100 mg, 0.23 mmol) was dissolved in reagent grade methanol (20 mL) and added aqueous potassium carbonate (20 mg in 5 mL water) and stirred for 2 hours at low temperature. The resulting reaction mixture was acidified to pH 4 using 1 N HCl and the precipitated product was filtered, dried and analyzed to the desired product (30 mg; 47% yield).

$^1$H NMR (300 MHz; CDCl$_3$): 0.87 δ (3 H, t, J=5.4 Hz); 1.85 δ (2 H, q, J=7.2 Hz); 3.6 δ (1 H, s); 3.6 δ (1 H, s); 5.42 δ (2 H, ABq, J$^1$=17.5 Hz; J$^2$=6.1 Hz); 5.61 δ (2 H, m); 6.15 δ (2 H, dd, J=12.8 Hz); 6.4 δ (1 H, d, J=2.5 Hz); 7.07 δ (1 H, s); 7.87 δ (1 H, t, J=7.2 Hz); 7.95 δ (1 H, t, J=7.9 Hz; 8.21 δ (1 H, d, J=8.4 Hz); 8.27 δ (1 H, d, J=6.2 Hz)

$^{13}$C NMR: δ 7.54, 30.31, 49.81, 65.21, 72.33, 96.88, 99.6, 119.48, 123.12, 125.69, 126.96, 130.63, 131.72, 137.2, 140.97, 143.14, 143.25, 145.31, 149.97, 156.55, 157.68, 172.36

FAB-MS: 373(M+1)

EXAMPLE 9

20-Acetoxy-7-(β-trimethylsilyl)ethynyl camptothecin

The 20-acetoxy-7-triflate (100 mg, 0.1855 mmol) was dissolved anhydrous and degassed anhydrous dimethylformamide (5 mL) and added zinc chloride (50.5 mg, 0.371 mmol). To it was then added tris(dibenzylideneacetonyl)bis palladium(0) (17 mg, 0.371 mmol), diisopropyl ethylamine (50 μL) followed by tri(2-furyl)phosphine (20 mg, 0.074 mmol). The resulting solution was stirred for approximately 30 minutes at room temperature. Then added propargylic trimethyl silane (0.1 mL). The reaction mixture was then stirred at room temperature for 48 hours. The resulting dark brown colored reaction mixture was then diluted with methylene chloride (25 mL), filtered, washed with water (15 mL). The crude product obtained after concentration is then flashed through a columnar bed of florisil, the fractions pooled, concentrated, dried under vacuum and analyzed.

$^1$H NMR (300 MHz; CDCl$_3$) 0.3 δ (9 H,s); 0.87 δ (3 H, t, J=5.4 Hz); 2.3 δ (2 H, q, J=7.2 Hz); 2.31 δ (3 H, s); 5.42 δ (2 H, ABq, J$^1$=17.5 Hz; J$^2$=6.1 Hz); 5.61 δ (2 H, m); 7.07 δ (1 H, s); 7.87 δ (1 H, t, J=7.2 Hz); 7.95 δ (1 H, t, J=7.9 Hz); 8.21 δ (1 H, d, J=8.4 Hz); 8.27 δ (1 H, d, J=6.2 Hz)

EXAMPLE 10

20-Acetoxy-7-methylthio camptothecin

The intermediate triflate (100 mg, 0.186 mmol) was dissolved in anhydrous 1,4-dioxane and cooled to 0° C. under a stream of argon. To it was then added diisopropyl ethylamine (0.1 mL; 0.557 mole) and slowly bubbled methanethiol for 5 minutes. The reaction mixture was then stirred under a balloon pressure for 15 hours. After 15 hours, the reaction mixture was diluted with methylene chloride (25 mL) and washed with water (20 mL×4), dried over anhydrous sodium sulfate, filtered and concentrated to obtain the crude product of the title compound in approximately 80.5% yield.

$^1$H NMR (300 MHz; CDCl$_3$): 0.87 δ (3 H, t, J=5.4 Hz); 2.31 δ (2 H, q, J=7.2 Hz); 2.28 δ (3 H, s); 2.31 δ (3 H, s); 5.42 δ (2 H, ABq, J$^1$=17.5 Hz; J$^2$=6.1 Hz); 5.61 δ (2 H, m); 7.07 δ (1 H, s); 7.65 δ (1 H, t, J=7.2 Hz); 7.75 δ (1 H, t, J=7.9 Hz); 8.1 δ (1 H, d, J=8.4 Hz); 8.61 d (1 H, d, J=6.2 Hz)

FAB-MS: 438 (M+1)

EXAMPLE 11

7-Methylthio camptothecin

20-Acetoxy-7-methylthio camptothecin (100 mg, 0.23 mmols) was dissolved in reagent grade methanol (20 mL) and added aqueous potassium carbonate (25 mg in 0.1 mL water) and stirred for about 3 hours at low temperature. The resulting reaction mixture was acidified with 1 N HCl to precipitate the lactone form of the compound. The precipitated product was then filtered, washed with water (10 mL×4) and with ether (10 mL), dried under vacuum. The pale yellow powder was then analyzed to the desired product (65 mg; 77% yield).

$^1$H NMR (300 MHz; CDCl$_3$): 0.87 δ (3 H, t, J=5.4 Hz); 2.28 δ (2 H, q, J=7.2 Hz); 2.31 δ (3 H, s); 3.6 δ (1 H, s); 5.42 δ (2 H, ABq, J$^1$=17.5 Hz; J$^2$ 6.1 Hz); 5.61 δ (2 H, s); 7.07 δ (1 H, s); 7.65 δ (1 H, t, J=7.2 Hz); 7.75 δ (1 H, t, J=7.9 Hz); 8.1 δ (1 H, d, J=8.4 Hz); 8.61 δ (1 H, d, J=6.2 Hz)

FAB-MS: 394 (M+1)

EXAMPLE 12

20-Acetoxy-7-methylsulfoxo camptothecin

20-Acetoxy-7-methylthio camptothecin (25 mg, 0.057 mmol) was dissolved in anhydrous methylene chloride (10 mL) and cooled to 0° C. using an ice bath under a stream of argon. Freshly purified m-chloroperbenzoic acid (10.3 mg, 1 equivalent) Was added, and the reaction mixture was stirred for 2 hours at low temperature. The reaction mixture was then diluted with methylene chloride (20 mL) and washed with water (10 mL×4), dried and concentrated to obtain the title compound in the crude form. The product was then flash chromatographed over a bed of florisil using 10% methanol in chloroform to furnish the desired sulfoxide as a diastereomeric mixture in 60% yield.

$^1$H NMR (300 MHz; CDCl$_3$): 0.87 δ (3 H, t, J=5.4 Hz); 2.29 δ (2 H, q, J=7.2 Hz); 2.31 δ (3 H, s); 3.32 δ (3 H, s); 5.42 δ (2 H, ABq, J$^1$=17.5 Hz; J$^2$=6.1 Hz); 5.61 δ (2 H, m); 7.07 δ (1 H, s); 7.65 δ (1 H, t, J=7.2 Hz); 7.75 δ (1 H, t, J=7.9 Hz); 8.1 δ (1 H, d, J=8.4 Hz); 8.61 δ (1 H, d, J=6.2 Hz)

FAB-MS: 454 (M+1)

EXAMPLE 13

7-Methylsulfoxol camptothecin

20-Acetoxy-7-methylsulfoxo camptothecin (100 mg, 0.18 mmols) was dissolved in reagent grade methanol (20 mL) and added aqueous potassium carbonate (25 mg in 0.1 mL water) and stirred for about 3 hours at low temperature. The resulting reaction mixture was acidified with 1 N HCl to precipitate the lactone form of the compound. The precipitated product was then filtered, washed with water (10 mL×4) and with ether (10 mL), dried under vacuum: The pale yellow powder was then analyzed to the desired product (65 mg; 61% yield).
$^1$H NMR (300 MHz; CDCl$_3$) 0.87 δ (3 H, t, J=5.4 Hz); 2.21 δ (2 H, q, J=7.2 Hz); 3.6 δ (1 H, s); 5.42 δ (2 H, ABq, J$^1$=17.5 Hz; J$^2$=6.1 Hz); 5.61 δ (2 H, m); 7.07 δ (1 H, s); 7.65 δ (1 H, t, J=7.2 Hz); 7.75 δ (1 H, t, J=7.9 Hz); 8.1 δ (1 H, d, J=8.4 Hz); 8.61 δ (1 H, d, J=6.2 Hz)
FAB-MS: 411 (M+1)

EXAMPLE 14

20-Acetoxy-7-ethylthio camptothecin

The intermediate triflate (100 mg, 0.186 mmol) was dissolved in anhydrous 1,4-dioxane and cooled to 0° C. under a stream of argon. To it was then added diisopropyl ethylamine (0.1 mL; 0.557 mole) and slowly added ethanethiol (0.4 mL) and then stirred the reaction mixture under a balloon pressure for 15 hours in a well ventilated hood. After 15 hours, the reaction mixture was diluted with methylene chloride (25 mL) and washed with water (20 mL×4), dried over anhydrous sodium sulfate, filtered and concentrated to obtain the crude product of the title compound in approximately 80.5% yield.
$^1$H NMR (300 MHz; CDCl$_3$): 0.87 δ (3 H, t, J=5.4 Hz) ; 1.26 δ (3 H, t, J=5.8 Hz); 2.21 δ (2 H, q, J=7.2 Hz); 2.31 δ (3 H, s); 2.28 δ (3 H, s); 3.19 δ (2 H, q, J=7.2 Hz); 3.6 δ (1 H, s); 5.42 δ (2 H, ABq, J$^1$=17.5 Hz; J$^2$=6.1 Hz); 5.61 δ (2 H, m); 7.07d (1 H, s); 7.65 δ (1 H, t, J=7.2 Hz); 7.75 δ (1 H, t, J=7.9 Hz); 8.1 δ (1 H, d, J=8.4 Hz); 8.58 δ (1 H, d, J=6.2 Hz)
FAB-MS: 468 (M+1)

EXAMPLE 15

7-Ethylthio camptothecin

20-Acetoxy-7-ethylthio camptothecin (100 mg, 0.21 mmol) was dissolved in reagent grade methanol (20 mL) and added aqueous potassium carbonate (25 mg in 0.1 mL water) and stirred for about 3 hours at low temperature. The resulting reaction mixture was acidified with 1 N HCl to precipitate the lactone form of the compound. The precipitated product was then filtered, washed with water (10 mL×4) and with ether (10 mL), dried under vacuum. The pale yellow powder was then analyzed to the desired product (69 mg; 76% yield).
$^1$H NMR (300 MHz; CDCl$_3$): 0.87 δ (3 H, t, J=5.4 Hz); 1.26 δ (3 H, t, J=5.8 Hz); 2.21 δ (2 H, q, J=7.2 Hz); 2.28 δ (3 H, s); 3.19 d (2 H, q, J=7.2 Hz); 3.6 d (1 H, s); 5.42 δ (2 H, ABq, J$^1$=17.5 Hz; J$^2$=6.1 Hz); 5.61 δ (2 H, m); 7.07 δ (1 H, s); 7.65 δ (1 H, t, J=7.2 Hz); 7.75 δ (1 H, t, J=7.9 Hz); 8.1 δ (1 H, d, J=8.4 Hz); 8.58 δ (1 H, d, J=6.2 Hz)
FAB-MS: 425 (M+1)

EXAMPLE 16

20-Acetoxy-7-isopropylthio camptothecin

The intermediate triflate (100 mg, 0.186 mmol) was dissolved in anhydrous 1,4-dioxane and cooled to 0° C. under a stream of argon. To it was then added diisopropyl ethylamine (0.1 mL; 0.557 mole) and slowly added isopropylthiol (1 mL). The reaction mixture was then stirred under a balloon pressure for 15 hours in a well ventilated hood. After 48 hours, the reaction mixture was diluted with methylene chloride (25 mL) and washed with water (20 mL×4), dried over anhydrous sodium sulfate, filtered and concentrated to obtain the crude product of the title compound in approximately 60.5% yield.
$^1$H NMR (300 MHz; CDCl$_3$): 0.87 δ (3 H, t, J=5.4 Hz); 1.26 δ (6 H, d, J=5.8 Hz); 2.19 δ (2 H, q, J=7.2 Hz); 2.31 δ (3 H, s); 2.28 δ (3 H, s); 3.59 δ (2 H, q, J=7.2 Hz); 5.42 δ (2 H, ABq, J$^1$=17.5 Hz; J$^2$=6.1 Hz); 5.61 δ (2 H, m); 7.07 δ (1 H, s); 7.65 δ (1 H, t, J=7.2 Hz); 7.75 δ (1 H, t, J=7.9 Hz); 8.1 δ (1 H, d, J=8.4 Hz); 8.58 (1H, d, J=6.2 Hz)
FAB-MS: 482 (M+1)

EXAMPLE 17

20-Acetoxy-7-phenylthio camptothecin

The intermediate triflate (100 mg, 0.186 mmol) was dissolved in anhydrous 1,4-dioxane and cooled to 0° C. under a stream of argon. To it was then added diisopropyl ethylamine (0.1 mL; 0.557 mole) and slowly added phenyl mercaptan (0.2 mL). The reaction mixture was then stirred under a balloon pressure for 15 hours in a well ventilated hood. After 48 hours, the reaction mixture was diluted with methylene chloride (25 mL) and washed with water (20 mL×4), dried over anhydrous sodium sulfate, filtered and concentrated to obtain the crude product of the title compound in approximately 80.5% yield.
$^1$H NMR (300 MHz; CDCl$_3$) : 0.87 δ (3 H, t, J=5.4 Hz); 2.19 δ (2 H, q, J=7.2 Hz) ; 2.28 δ (3 H, s); 4.82 δ (2 H, ABq, J$^1$=17.5 Hz; J$^2$=6.1 Hz); 5.61 δ (2 H, s); 6.93–7.61 δ (5 H, m); 7.07 δ (1 H, s); 7.65 δ (1 H, t, J=7.2 Hz); 7.75 δ (1 H, t, J=7.9 Hz); 8.1 δ (1 H, d, J=8.4 Hz); 8.61 δ (1 H, d, J=6.2 Hz)
$^{13}$C NMR: δ 7.32, 20.56, 31.63, 50.08, 66.91, 66.98, 75.43, 95.97, 120.47, 125.46, 127.14, 127.49, 128.5, 128.55, 128.72, 129.07, 129.92, 130.15, 130.99, 131.12, 131.56, 140.19, 145.76, 146.11, 149.23, 152.03, 157.07, 167.59, and 169.94
FAB-MS (M+1): 500

EXAMPLE 18

7-Phenylthio camptothecin

20-Acetoxy-7-phenylthio camptothecin (100 mg, 0.21 mmol) was dissolved in reagent grade methanol (20 mL), aqueous potassium carbonate (25 mg in 0.1 mL water) was added, and the solution stirred for about 3 hours at low temperature. The resulting reaction mixture was acidified with 1 N HCl to precipitate the lactone form of, the compound. The precipitated product was then filtered, washed with water (10 mL×4) and with ether (10 mL), and then dried under vacuum. The pale yellow powder was then analyzed to the desired product (79 mg; 80% yield).
$^1$H NMR (300 MHz; CDCl$_3$): 0.87 δ (3 H, t, J=5.4 Hz); 1.89 δ (2 H, q, J=7.2 Hz); 3.6 δ (1 H, s); 4.82 δ (2 H, ABq, J$^1$=17.5 Hz; J$^2$=6.1 Hz); 5.61 δ (2 H, s); 6.93–7.61 δ (5 H, m); 7.07 δ (1 H, s); 7.65 δ (1 H, t, J=7.2 Hz); 7.75 δ (1 H, t, J=7.9 Hz); 8.1 δ (1 H, d, J=8.4 Hz); 8.61 δ (1 H, d, J=6.2 Hz)
$^{13}$C NMR: δ 7.32, 20.56, 31.63, 50.08, 66.91, 66.98, 75.43, 95.97, 120.47, 125.46, 127.14, 127.49, 128.5, 128.55, 128.72, 129.07, 129.92, 130.15, 130.99, 131.12, 131.56, 140.19, 145.76, 146.11, 149.23, 152.03, 157.07, 167.59, and 169.94
FAB-MS (M+1): 457

EXAMPLE 19

20-Acetoxy-7-(4-fluorophenyl)thio camptothecin

The intermediate triflate (100 mg, 0.186 mmol) was dissolved in anhydrous 1,4-dioxane and cooled to 0° C.

under a stream of argon. To it was then added diisopropyl ethylamine (0.1 mL; 0.557 mole) and slowly added 4-fluorophenyl mercaptan (0.2 mL). The reaction mixture was then stirred under a balloon pressure for 15 hours in a well ventilated hood. After 48 hours, the reaction mixture was diluted with methylene chloride (25 mL) and washed with water (20 mL×4), dried over anhydrous sodium sulfate, filtered and concentrated to obtain the crude product of the title compound in approximately 80.5% yield.

$^1$H NMR (300 MHz; CDCl$_3$) : 0.87 δ (3 H, t, J=5.4 Hz) ; 2.19 δ (2 H, q, J=7.2 Hz); 2.28 δ (3 H, s); 4.82 δ (2 H, ABq, J$^1$=17.5 Hz; J$^2$=6.1 Hz); 5.61 δ (2 H, m); 6.93–7.61 δ (4 H, m); 7.07 (1 H, s); 7.65 δ (1 H, t, J=7.2 Hz); 7.75 δ (1 H, t, J=7.9 Hz); 8.1 δ (1 H, d, J=8.4 Hz); 8.61 δ (1 H, d, J=6.2 Hz)

$^{13}$C NMR: δ 7.42, 31.63, 50.08, 66.01, 66.98, 72.49, 98.01, 116.92, 117.21, 118.84, 125.12, 128.38, 128.52, 130.43, 130.84, 131.48, 133.19, 133.3, 139.69, 146.17, 149.36, 149.36, 149.98, 152.07, 160.99 and 173.82

FAB-MS (M+1): 518

EXAMPLE 20

7-(4-fluorophenyl)thio camptothecin

20-Acetoxy-7-(4-fluorophenyl) thio camptothecin (100 mg, 0.21 mmol) was dissolved in reagent grade methanol (20 mL) and added aqueous potassium carbonate (25 mg in 0.1 mL water), and stirred for about 3 hours at low temperature. The resulting reaction mixture was acidified with 1 N HCl to precipitate the lactone form of the compound. The precipitated product was then filtered, washed with water (10 mL×4) and with ether (10 mL), and dried under vacuum. The pale yellow powder was then analyzed to confirm the desired product (79 mg; 80% yield).

$^1$H NMR (300 MHz; CDCl$_3$): 0.87 δ (3 H, t, J=5.4 Hz); 2.23 δ (2 H, q, J=7.2 Hz); 3.6 δ (1 H, s); 4.82 δ (2 H, ABq, J$^1$=17.5 Hz; J$^2$=6.1 Hz); 5.61 δ (2 H, s); 6.93–7.61 δ (4 H, m); 7.07 δ (1 H, s); 7.65 δ (1 H, t, J=7.2 Hz); 7.75 δ (1 H, t, J=7.9 Hz); 8.1 δ (1 H, d, J=8.4 Hz); 8.61 δ (1 H, d, J=6.2 Hz)

$^{13}$C NMR: δ 7.42, 31.63, 50.08, 66.01, 66.98, 72.49, 98.01, 116.92, 117.21, 118.84, 125.12, 128.38, 128.52, 130.43, 130.84, 131.48, 133.19, 133.3, 139.69, 146.17, 149.36, 149.36, 149.98, 152.07, 160.99 and 173.82

FAB-MS (M+1): 475

EXAMPLE 21

20-Acetoxy-7-trimethylsilyl camptothecin

Hexamethyl disilane (62 μL, 0.3 mmol) was taken up in a flame dried round bottom flask under argon. To it was added anhydrous hexamethyl phosphoramide (0.5 mL) and anhydrous tetrahydrofuran at room temperature. The reaction medium was then cooled to 0° C. using an ice bath and methyllithium was introduced (220 μL, estimated as 30.8 mg per mL). The dark colored solution was then stirred at low temperature for 20 to 30 minutes. Copper(I) iodide 42 mg, 0.22 mmol) was taken up in a separate predried round bottom flask and added anhydrous tetrahydrofuran (4 mL) to form a suspension of the copper iodide. To this suspension was then added tri-n-butyl phosphine (117 μL, 0.47 mmol) and the mixture stirred at room temperature for one hour. The resulting homogenous colorless solution was then cooled to 0° C. and transferred to the above organolithium reagent prepared using a cannula at −78° C. The reaction medium was then stirred for the next 15 to 20 minutes. The ongoing intermediate triflate synthon (114 mg, 0.213 mmol) was taken up in anhydrous tetrahydrofuran under a blanket of purified argon and then transferred to the above cuprate reagent at −78° C. The dark reaction solution was then stirred for 15 hours and then quenched with saturated ammonium chloride solution. The organic soluble portion was then taken up in chloroform (25 mL). The aqueous portion was then repeatedly extracted with chloroform (25 mL×3). The combined organic portion was then dried over with anhydrous sodium sulfate, filtered and concentrated to yield the desired product in the crude form. The crude form was then flash chromatographed over a bed of silica gel using 10% methanol in chloroform to obtain the title compound in 75% yield.

$^1$H NMR (300 MHz; CDCl$_3$): 0.645 δ (9 H, s); 0.90 δ (3 H, t, J=5.4 Hz); 2.12 δ (2 H, q, J=7.2 Hz); 2.21 δ (3 H, s); 2.23 δ (3 H, s); 5.42 δ (2 H, ABq, J$^1$=17.5 Hz; J$^2$=6.1 Hz); 5.49 δ (2 H, q, J=2.5 Hz); 7.12 δ (1 H, s); 7.87 δ (1 H, t, J=7.2 Hz); 7.95 δ (1 H, t, J=7.9 Hz); 8.21 δ (1 H, d, J=5.4 Hz); 8.27 δ (1 H, d, J=5.2 Hz)

$^{13}$C NMR: δ 1.03, 7.58, 30.23, 51.7, 65.23, 72.36, 96.43, 96.43, 118.88, 127.51, 128.31, 128.70, 129.69, 130.48, 131.44, 135.95, 143.46, 145.42, 147.20, 150.15, 156.74; 172.58

FAB-MS: 464 (M+1)

EXAMPLE 22

7-Trimethylsilyl camptothecin

20-Acetoxy-7-trimethylsilyl camptothecin (100 mg, 0.21 mmol) was dissolved in reagent grade methanol (20 mL) and added aqueous potassium carbonate (25 mg in 0.1 mL water), and stirred for about 3 hours at room temperature. The resulting reaction mixture is then cooled to 5° C. and acidified with 1 N HCl to precipitate the lactone form of the compound. The precipitated product was then filtered, washed with water (10 mL×4) and with ether (10 mL), and dried under vacuum. The pale yellow powder was then analyzed to confirm the desired product (60 mg; 63% yield).

$^1$H NMR (300 MHz; CDCl$_3$): 0.645 δ (9 H, s) ; 0.90 δ (3 H, t; J=5.4 Hz); 2.12 δ (2 H, q, J=7.2 Hz); 2.23 δ ( 3 H, s); 3.6 δ (1 H, s); 5.42 δ (2 H, ABq, J$^1$=17.5 Hz; J$^2$=6.1 Hz); 5.49 δ (2 H, q, J=2.5 Hz); 7.12 δ (1 H, s); 7.87 δ (1 H, t, J=7.2 Hz); 7.95 δ (1 H, t, J=7.9 Hz); 8.21 δ (1 H, d, J=5.4 Hz); 8.27 δ (1 H, d, J=5.2 Hz)

$^{13}$C NMR: δ 1.03, 7.58, 30.23, 51.7, 65.23, 72.36, 96.43, 96.43, 118.88, 127.51, 128.31, 128.70, 129.69, 130.48, 131.44, 135.95, 143.46, 145.42, 147.20, 150.15, 156.74, 172.58

FAB-MS: 421 (M+1)

EXAMPLE 23

20-Acetoxy-7-(β-trimethylsilyl)ethynyl camptothecin

The 20-acetoxy-7-triflate (100 mg, 0.1855 mmol) was dissolved anhydrous and degassed anhydrous dimethylformamide (5 mL) and added zinc chloride (50.5 mg, 0.371 mmol). To it was then added tris(dibenzylideneacetonyl)bis palladium(0) (17 mg, 0.371 mmol) followed by tri(2-furyl) phosphine (20 mg, 0.074 mmol). The resulting solution was stirred for approximately 30 minutes at room temperature, then acetylenic trimethylsilane (0.1 mL) was added. The reaction mixture was then stirred at room temperature for 48 hours. The resulting dark brown colored reaction mixture was then diluted with methylene chloride (25 mL), filtered, and washed with water (15 mL). The crude product obtained after concentration is then flashed through a columnar bed of florisil, the fractions pooled, concentrated, dried under vacuum and analyzed.

¹H NMR (300 MHz; CDCl₃): 0.45 δ (9 H, s); 0.87 δ (3 H, t, J=5.4 Hz); 1.85 δ (2 H, q, J=7.2 Hz); 2.31 δ (3 H, s); 5.42 δ (2 H, ABq, J¹=17.5 Hz; J²=6.1 Hz); 5.61 δ (2 H, m); 7.07 δ (1 H, s); 7.87 δ (1 H, t, J=7.2 Hz); 7.95 δ (1 H, t, J=7.9 Hz); 8.21 δ (1 H, d, J=8.4 Hz); 8.27 δ (1 H, d, J=6.2 Hz)
FAB-MS (M+1): 501

EXAMPLE 24

20-Acetoxy-7-ethynyl camptothecin

20-Acetoxy-7-trimethylsilylethynyl camptothecin (100 mg, 0.21 mmol) was dissolved in reagent grade methanol (20 mL) and added aqueous potassium carbonate (25 mg in 0.1 mL water) and stirred for about 15 minutes at low temperature. The resulting reaction mixture was then cooled to 5° C. and acidified with 1 N HCl to precipitate the lactone form of the compound. The precipitated product was then filtered, washed with water (10 mL×4) and with ether (10 mL), and dried under vacuum. The pale yellow powder was then analyzed to confirm the desired product (40 mg; 53% yield).
¹H NMR (300 MHz; CDCl₃): 0.90 δ (3 H, t, J=5.4 Hz); 2.12 δ (2 H, q, J=7.2 Hz); 2.23 δ (3 H, s); 3.6 δ (1 H, s); 4.06 δ (1 H, s); 5.42 d (2 H, ABq, J¹=17.5 Hz; J²=6.1 Hz); 5.49 δ (2 H, q, J=2.5 Hz); 7.12 δ (1 H, s); 7.87 δ (1 H, t, J=7.2 Hz); 7.95 δ (1 H, t, J=7.9 Hz); 8.21 δ (1 H, d, J=5.4 Hz); 8.47 δ (1 H, d, J=5.2 Hz)

EXAMPLE 25

7-Ethynyl camptothecin

20-Acetoxy-7-ethynyl camptothecin (50 mg, 0.11 mmol) was dissolved in reagent grade methanol (5 mL) and added aqueous potassium carbonate (25 mg in 0.1 mL water), and then stirred for about 2 hours at low temperature. The resulting reaction mixture was then cooled to 5° C. and acidified with 1 N HCl to precipitate the lactone form of the compound. The precipitated product was then filtered, washed with water (10 mL×4) and with ether (10 mL), and dried under vacuum. The pale yellow powder was then analyzed to confirm the desired product (60 mg; 63% yield).
¹H NMR (300 MHz; CDCl₃):0.90 δ (3 H, t, J=5.4 Hz) ; 2.12 δ (2 H, q, J=7.2 Hz); 3.6 δ (1 H, s); 4.06 δ (1 H, s); 5.42 δ (2 H, ABq, J¹=17.5 Hz; J²=6.1 Hz); 5.49 δ (2 H, q, J=2.5 Hz); 7.12 δ (1 H, s); 7.87 δ (1 H, t, J=7.2 Hz); 7.95 δ (1 H, t, J=7.9 Hz); 8.21 δ (1 H, d, J=5.4 Hz); 8.47 δ (1 H, d, J=5.2 Hz)

EXAMPLE 26

7-(β-trimethylsilyl)ethyl camptothecin

Camptothecin (500 mg, 1.44 mmol) was suspended in deionized water (10 mL) and freshly distilled 3-trimethylsilyl-1 propanal (3.0 mL; excess) followed by dropwise addition of concentrated sulfuric acid (5.5 mL) at 0° C. using an ice bath over a period of 15 min. To the above stirred reaction medium was then introduced a 30% aqueous solution of hydrogen peroxide (2 mL) followed by iron sulfate heptahydrate (156 mg) in 1 mL water. The reaction mixture was then stirred at 25° C. for an additional 24 hours. The reaction mixture was then diluted with ice-cold water and extracted with chloroform (50 mL×3). The combined organic portion was then dried over anhydrous sodium sulfate, filtered and concentrated to obtain the crude product in 65% yield. The crude product was then purified over a silica gel column using 90% chloroform/methanol mixture to furnish 0.46 g of the title compound (54% yield).
¹H NMR (300 MHz; CDCl₃): 0.01 δ (9 H, s) ; 0.48 δ (2 H, q, J=4.8 Hz); 0.90 δ (3 H, t, J=5.4 Hz); 1.53 δ (2 H, q, J=6.6 Hz); 2.12 δ (2 H, q, J=7.2 Hz); 2.23 δ (3 H, s); 3.6 d (1 H, s); 5.42 δ (2 H, ABq, J¹=17.5 Hz; J²=6.1 Hz); 5.49 δ (2 H, q, J=2.5 Hz); 7.12 δ (1 H, s); 7.87 δ (1 H, t, J=7.2 Hz); 7.95 δ (1 H, t, J=7.9 Hz); 8.21 δ (1 H, d, J=5.4 Hz); 8.27 (1 H, d, J=5.2 Hz)
¹³C NMR: δ 1.03, 7.58, 9.62, 23.48, 30.23, 51.7, 65.23, 72.36, 96.43, 96.43, 118.88, 127.51, 128.31, 128.70, 129.69, 130.48, 131.44, 135.95, 143.46, 145.42, 147.20, 150.15, 156.74, 172.58
FAB-MS: 492 (M+1)

EXAMPLE 27

20-Acetoxy-7-(β-trimethylsilyl)ethylthio camptothecin

The intermediate triflate (100 mg, 0.186 mmol) was dissolved in anhydrous 1,4-dioxane and cooled to 0° C. under a stream of argon. To it was then added diisopropyl ethylamine (0.1 mL; 0.557 mole), and slowly added trimethylsilyl ethanethiol (0.25 mL). The reaction mixture was then stirred under a balloon pressure of argon for 15 hours in a well ventilated hood. After 15 hours, the reaction mixture was diluted with methylene chloride (25 mL) and washed with water (20 mL×4), dried over anhydrous sodium sulfate, filtered and concentrated to obtain the crude product of the title compound in approximately 80% yield.
¹H NMR (300 MHz; CDCl₃) : 0.01 δ (9 H, s); 0.87 δ (3 H, t, J=5.4 Hz); 0.98 δ (2 H, q, J=4.8 Hz); 1.26 δ (3 H, t, J=5.8 Hz); 1.89 δ (2 H, q, J=7.2 Hz); 2.31 δ (3 H, s); 2.28 d (3 H, s); 3.05 δ (2 H, q, J=5 Hz); 3.19 δ (2 H, q, J=7.2 Hz); 5.42 δ (2 H, ABq, J¹=17.5 Hz; J²=6.1 Hz); 5.61 δ (2 H, s); 7.07 δ (1 H, s); 7.65 δ (1 H, t, J=7.2 Hz); 7.75 δ (1 H, t, J=7.9 Hz); 8.1 δ (1 H, d, J=8.4 Hz); 8.58 δ (1 H, d, J=6.2 Hz)
FAB-MS: 523(M+1 )

EXAMPLE 28

7-(β-trimethylsilyl)ethylthio camptothecin

20-Acetoxy-7-ethylthio camptothecin (100 mg, 0.21 mmol) was dissolved in reagent grade methanol (20 mL) and added aqueous potassium carbonate (25 mg in 0.1 mL water) and stirred for about 3 hours at low temperature. The resulting reaction mixture was acidified with 1 N HCl to precipitate the lactone form of the compound. The precipitated product was then filtered, washed with water (10 mL×4) and with ether (10 mL), and then dried under vacuum. The pale yellow powder was then analyzed to confirm the desired product (69 mg; 76% yield).
¹H NMR (300 MHz; CDCl₃): 0.01 δ (9 H, s); 0.87 δ (3 H, t, J=5.4 Hz); 0.98 δ (2 H, q, J=4.8 Hz); 1.26 δ (3 H, t, J=5.8 Hz); 1.89 δ (2 H, q, J=7.2 Hz); 2.31 δ (3 H, s); 2.28 δ (3 H, s); 3.05 δ (2 H, q, J=5 Hz); 3.19 δ (2 H, q, J=7.2 Hz); 3.6 δ (1 H, s); 5.42 δ (2 H, ABq, J¹=17.5 Hz; J²=6.1 Hz); 5.61 δ (2 H, s); 7.07 δ (1 H, s); 7.65 δ (1 H, t, J=7.2 Hz); 7.75 δ (1 H, t, J=7.9 Hz); 8.1 δ (1 H, d, J=8.4 Hz); 8.58 δ (1 H, d, J=6.2 Hz)
FAB-MS: 481 (M+1)

EXAMPLE 29

20-Acetoxy-7-(α-trimethylsilyl)methylthio camptothecin

The intermediate triflate (100 mg, 0.186 mmol) was dissolved in anhydrous 1,4-dioxane (2 mL) and cooled to 0°

C. under a stream of argon. To it was then added diisopropyl ethylamine (0.1 mL; 0.557 mole) and slowly added trimethylsilyl methanethiol (0.2 mL). The reaction mixture was then stirred under a balloon pressure of argon for 15 hours in a well ventilated hood. After 48 hours, the reaction mixture was diluted with methylene chloride (25 mL) and washed with water (20 mL×4), dried over anhydrous sodium sulfate, filtered and concentrated to obtain the crude product of the title compound in approximately 70% yield.

$^1$H NMR (300 MHz; CDCl$_3$): 0.15 δ (9 H, s); 0.87 δ (3 H, t, J=5.4 Hz); 1.26 δ (3 H, t, J=5.8 Hz); 2.21 δ (3 H, s); 2.19 δ (2 H, q, J=7.2 Hz); 2.31 δ (2 H, s); 2.38 δ (2 H, s); 5.42 δ (2 H, ABq, J$^1$=17.5 Hz; J$^2$=6.1 Hz); 5.61 δ (2 H, s); 7.07 δ (1 H, s); 7.65 d (1 H, t, J=7.2 Hz); 7.75 d (1 H, t, J=7.9 Hz); 8.22 δ (1 H, d, J=8.4 Hz); 8.55 δ (1 H, d, J=6.2 Hz)

FAB-MS: 509(M+1)

EXAMPLE 30

7-(α-trimethylsilyl)methylthio camptothecin

20-Acetoxy-7-methylthio camptothecin (100 mg, 0.21 mmol) is dissolved in reagent grade methanol (20 mL) and added aqueous potassium carbonate (25 mg in 0.1 mL water), and stirred for about 3 hours at low temperature. The resulting reaction mixture was acidified with 1 N HCl to precipitate the lactone form of the compound. The precipitated product was then filtered, washed with water (10 mL×4) and with ether (10 mL), and dried under vacuum. The pale yellow powder was then analyzed to confirm the desired product (59 mg; 67% yield).

$^1$H NMR (300 MHz; CDCl$_3$): 0.15 δ (9 H, s); 0.87 δ (3 H, t, J=5.4 Hz); 1.26 δ (3 H, t, J=5.8 Hz); 2.19 δ (2 H, q, J=7.2 Hz); 2.28 δ (2 H, s); 2.38 δ (2 H, s); 3.6 δ (1 H, s); 5.42 δ (2 H, ABq, J$^1$=17.5 Hz; J$^2$=6.1 Hz); 5.61 δ (2 H, s); 7.07 δ (1 H, s); 7.65 δ (1 H, t, J=7.2 Hz); 7.75 δ (1 H, t, J=7.9 Hz); 8.1 δ (1 H, d, J=8.4 Hz); 8.58 δ (1 H, d, J=6.2 Hz)

FAB-MS: 467 (M+1)

EXAMPLE 31

20-Dehydroxy camptothecin

Camptothecin (500 mg, 1.44 mmol) was suspended in 1,4-dioxane (10 mL) and added Lawsson's reagent (290.5 mg, 0.72 mmol). The reaction mixture was then heated to 90° C. for 10 hours under an inert atmosphere. The resultant homogeneous reaction mixture was then concentrated, organic portion was taken up in chloroform (25 mL) and the aqueous fraction was repeatedly extracted with chloroform (25 mL×3). The combined organic portion was then concentrated to get the title compound in the crude form. The crude product was then flash chromatographed over a bed of florisil using 10% chloroform in methanol to furnish the desired product in 40% yield in diastereomeric mixture.

$^1$H NMR (300 MHz; CDCl$_3$): 1.07 δ (3 H, t, J=5.4 Hz); 2.12 δ (2 H, q, J=7.2 Hz); 3.69 δ (1 H, t, J=6.6 Hz); 5.42 δ (2 H, ABq, J$^1$=17.5 Hz; J$^2$=6.1 Hz); 5.59 δ (2 H, q, J=2.5 Hz); 7.62 δ (1 H, s); 7.71 δ (1 H, t, J=7.2 Hz); 7.85 δ (1 H, t, J=7.9 Hz); 8.01 δ (1 H, d, J=5.4 Hz); 8.23 δ (1 H, d, J=5.2 Hz); 8.47 δ (1 H, s)

$^{13}$C NMR: δ 11.1, 25.25, 29.6, 45.81, 49.93, 66.04, 99.76, 120.79, 128.10, 128.24, 128.72, 129.8, 130.73, 131.2, 146.12, 147.27, 149.06, 158.01 and 171.01

FAB (M+l): 361.2

EXAMPLE 32

20-Acetoxy-7-(γ-trimethylsilyl)-propen-α-yl camptothecin

The 20-acetoxy-7-triflate (100 mg, 0.1855 mmol) was dissolved anhydrous and degassed anhydrous dimethylformamide (5 mL) and added zinc chloride (50.5 mg, 0.371 mmol). To it was then added tris(dibenzylideneacetonyl)bis palladium(0) (17 mg, 0.371 mmol) followed by tri(2-furyl)phosphine (20 mg, 0.074 mmol). The resulting solution was stirred for approximately 30 minutes at room temperature, then propargylic trimethylsilane (0.1 mL) was added. The reaction mixture was then stirred at room temperature for 48 hours. The resulting dark brown colored reaction mixture was then diluted with methylene chloride (25 mL), filtered, washed with water (15 mL). The crude product obtained after concentration was then flashed through a columnar bed of florisil, the fractions pooled, concentrated, dried under vacuum and analyzed.

$^1$H NMR (300 MHz; CDCl$_3$): 0.26 δ (9 H, s) ; 0.97 δ (3 H, t, J=5.4 Hz); 2.02 δ (2 H, s); 2.24 δ (2 H, q, J=7.2 Hz); 2.21 δ (3 H, s); 5.42 δ (2 H, ABq, J$^1$=17.5 Hz; J$^2$=6.1 Hz); 5.61 δ (2 H, m); 7.2 δ (1 H, s); 7.77 δ (1 H, t, J=7.2 Hz); 7.85 δ (1 H, t, J=7.9 Hz); 8.21 δ (1 H, d, J=8.4 Hz); 8.32 δ (1 H, d, J=6.2 Hz)

FAB-MS (M+1): 501

EXAMPLE 33

20-Acetoxy-7-(propen-α-yl) camptothecin

20-Acetoxy-7-[(γ-trimethylsilyl) -propen-α-yl] camptothecin (100 mg, 0.21 mmol) was dissolved in reagent grade methanol (20 mL) and added aqueous potassium carbonate (25 mg in 0.1 mL water), and then stirred for about 15 minutes at low temperature. The resulting reaction mixture was then cooled to 5° C. and acidified with 1 N HCl to precipitate the lactone form of the compound. The precipitated product was then filtered, washed with water (10 mL×4) and with ether (10 mL), dried under vacuum. The pale yellow powder was then analyzed to the desired product (40 mg; 53% yield).

$^1$H NMR (300 MHz; CDCl$_3$): 0.97 δ (3 H, t, J=5.4 Hz); 2.02 δ (2 H, s); 2.24 δ (2 H, q, J=7.2 Hz); 2.21 δ (3 H, s); 5.42 δ (2 H, ABq, J$^1$=17.5 Hz; J$^2$=6.1 Hz); 5.61 δ (2 H, m); 7.2 δ (1 H, s); 7.77 δ (1 H, t, J=7.2 Hz); 7.85 δ (1 H, t, J=7.9 Hz); 8.21 δ (1 H, d, J=8.4 Hz); 8.32 δ (1 H, d, J=6.2 Hz)

EXAMPLE 34

7-(γ-trimethylsilyl)propen-α-yl camptothecin

20-Acetoxy-7-(γ-trimethylsilyl)propen-α-yl camptothecin (50 mg, 0.11 mmol) was dissolved in reagent grade methanol (5 mL) and added aqueous potassium carbonate (25 mg in 0.1 mL water) and stirred for about 2 hours at low temperature. The resulting reaction mixture was then cooled to 5° C. and acidified with 1 N HCl to precipitate the lactone form of the compound. The precipitated product was then filtered, washed with water (10 mL×4) and with ether (10 mL), dried under vacuum. The pale yellow powder was then analyzed as the desired product (60 mg; 63% yield) and 10% of the isomerized congener the corresponding 7-allenic derivative.

$^1$H NMR (300 MHz; CDCl$_3$): 0.26 δ (9 H, s); 0.97 δ (3 H, t, J=5.4 Hz); 2.02 δ (2 H, s, corresponds to the acetylenic counterpart); 2.24 δ (2 H, q, J=7.2 Hz); 5.42 δ (2 H, ABq, J$^1$=17.5 Hz; J$^2$=6.1 Hz); 5.6 δ (2 H, m); 7.2 δ (1 H, s); 7.77 δ (1 H, t, J=7.2 Hz); 7.85 δ (1 H, t, J=7.9 Hz); 8.21 δ (1 H, d, J=8.4 Hz); 8.32 δ (1 H, d, J=6.2 Hz)

EXAMPLE 35

20-Dehydroxy-7-Ethyl-camptothecin

7-Ethyl camptothecin (456 mg, 1.213 mmol) was suspended in 1,4-dioxane (10 mL) and added Lawsson's reagent (5 mg, 0.665 mmol). The reaction mixture was then heated to 90° C. for 10 hours under an inert atmosphere. The resultant homogeneous reaction mixture was then concentrated, the organic portion was taken up in chloroform (25 mL) and the aqueous fraction was repeatedly extracted with chloroform (25 mL×3). The combined organic portion was then concentrated to get the title compound in the crude form. The crude product was then flash chromatographed over a bed of florisil using 10% chloroform in methanol to furnish the desired product in 40% yield in diastereomric mixture.

$^1$H NMR (300 MHz; CDCl$_3$): 1.08 δ (3 H, t, J=5.4 Hz) ; 2.38 δ (3 H, t, J=5.4 Hz; 2.1 δ (2 H, q, J=7.2 Hz); 3.19 δ (2 H, q, J=7.8 Hz); 3.69 δ (1 H, t, J=6.6 Hz); 5.42 δ (2 H, ABq, J$^1$=17.5 Hz; J$^2$=6.1 Hz); 5.59 δ (2 H, q, J=2.5 Hz); 7.62 δ (1 H, s); 7.71 δ (1 H, t, J=7.2 Hz); 7.85 δ (1 H, t, J=7.9 Hz); 8.12 δ (1 H, d, J=5.4 Hz); 8.20 δ (1 H, d, J=5.2 Hz)

$^{13}$C NMR: δ 11.13, 13.87, 22.91, 25.25, 45.75, 49.20, 65.97, 99.56, 120.45, 123.52, 126.85, 127.02, 130.12, 130.6, 145.79, 146.76, 147.25, 149.97, 151.95, 157.97, 171.01 FAB (M+1): 389.1

EXAMPLE 36

N-Acetyl-1,2,3,4-tetrahydrocamptothecin

Camptothecin purchased from China was further purified by recrystallization, using reagent grade dimethylformamide as solvent preferably at a concentration at about 1 g of camptothecin in 10 to 15 mL of dimethylformamide and warming to approximately 130° C. Platinum catalyst was generated in situ. Platinum oxide (2.0 g) in glacial acetic acid (200 mL) was stirred under a blanket of hydrogen (1 atm) at room temperature for about an hour. Camptothecin (10.0 g, 0.023 mole) and additional acetic acid (300 mL) were added to the above suspension. The mixture was then agitated vigorously under hydrogen for another 3.5 hours (consumption of about 1.0 L of hydrogen was measured). The solution was transferred into another flask under nitrogen. Solvent was removed under high vacuum at room temperature to give 12.7 g of crude tetrahydrocamptothecin intermediate.

To the above tetrahydrocamptothecin (12.1 g) without any further purification or isolation was then slowly added excess acetyl chloride (50 mL). The suspension generated was then stirred under an inert atmosphere at ambient temperature overnight. Excess acetyl chloride was evaporated in vacuo. The residue was dissolved in chloroform, washed with brine and dried over anhydrous sodium sulfate. Solvent was removed to give 10.3 g of crude 1-acetyl-20-acetoxy tetrahydrocamptothecin. A portion of the crude product (4.8 g) was subsequently purified over silica bed by flash column using ethyl acetate-methanol mixture. The isomeric mixture of crude 1-acetyl-20-acetoxy tetrahydrocamptothecin was isolated (3.05 g, 53.5% yield from camptothecin) as off-white crystals.

$^1$H NMR (250 MHz Varian; CDCl$_3$) : 0.89 δ (3 H, t, J=6.25 Hz); 1.91–2.21 δ (2 H, m); 2.09 δ (3 H, s); 2.69–2.91 δ (2 H, ABq, J$_1$=1.75 Hz; J2=4.25 Hz); 3.41 δ (1 H, dd, J=5.75 Hz); 3.58 δ (1 H, m); 2.55 δ (1 H, dd, J=7.75 Hz); 5.24 δ (1 H; ABq, J$_{1,2}$=14.25 Hz); 6.3 δ (1 H, s); 6.49 δ (1 H, d, J=8.5 Hz); 6.81 δ (1 H, m); 7.18–7.25 δ (3 H, m)

EXAMPLE 37

1-acetyl-10-Nitro-tetrahydrocamptothecin 1-acetyl-20-acetoxy tetrahydrocamptothecin (1.786 g, 4.1 mmol) in 25 mL concentrated sulfuric acid was cooled in an acetone-ice bath. 3.0 mL of fuming nitric acid was added dropwise to the above thick solution while maintaining vigorous stirring. After 60 minutes in the ice, the reaction product was extracted out using chloroform. The organic portion was washed with sodium bicarbonate aqueous solution, brine and dried over sodium sulfate. Solvent was removed to give 1.11 g of 10-nitro-1-acetyl tetrahydrocamptothecin (61% yield).

$^1$H NMR (250 MHz Varian; CDCl$_3$): 0.89 δ (3 H, t, J=6.25 Hz); 1.91–2.21 δ (2 H, m); 2.09 δ (3 H, s); 2.69–2.91 δ (2 H, ABq, J$_1$=1.75 Hz; J2=4.25 Hz); 3.41 δ (1 H, dd, J=5.75 Hz); 3.58 δ (1 H, m); 2.55 δ (1 H, dd, J=7.75 Hz); 5.24 δ (1 H; ABq, J$_{1,2}$=14.25 Hz); 6.49 δ (1 H, d, J=8.5 Hz); 6.66 δ (1 H, s); 7.12 δ (1 H, d, J=7 Hz); 7.18–7.25 δ (3 H, m)

EXAMPLE 38

1-Acetyl-10-Amino-tetrahydrocamptothecin

To the ongoing nitro intermediate (3.43 g, 7.7 mmol) and platinum oxide (0.5 g) in methanol (400 mL), hydrogen was then bubbled for approximately 3 hours. The catalyst was then filtered while keeping the magma wet and the solvent was removed over aspirator vacuum to deliver the 10-amino title compound in quantitative yield.

$^1$H NMR (250 MHz Varian; CDCl$_3$): 0.89 δ (3 H, t, J=6.25 Hz) 1.91–2.21 δ (2 H, m); 2.09 δ (3 H, s); 2.69–2.91 δ (2 H, ABq, J$_1$=1.75 Hz; J2=4.25 Hz); 3.41 δ (1 H, dd, J=5.75 Hz); 3.58 δ (1 H, m); 2.55 δ (1 H, dd, J=7.75 Hz); 5.24 δ (1 H; ABq, J$_{1,2}$=14.25 Hz); 6.59–6.72 δ (5 H, d, J=8.5 Hz)

EXAMPLE 39

1-Acetyl-10-Fluoro-tetrahydrocamptothecin

A solution of 10-amino-1-acetyl tetrahydrocamptothecin (1.28 g, 3.1 mmol) in 300 mL chloroform was cooled down in acetone-ice bath (−15° C.). Boron trifluoride diethyl etherate (1.5 mL, 1.5 equiv.) in 7 mL was then slowly added. After the addition, the mixture was allowed to warm to room temperature. After stirring about 15 minutes the mixture was cooled back in acetone-ice bath. t-Butyl nitrite (0.54 mL, 1.5 equiv.) in 30 mL chloroform was added dropwise. The mixture was stirred in ice bath for 30 minutes and then warmed to room temperature for 60 minutes. Solvent was removed in vacuo. To the residue was added 20 mL toluene and heated to 100–110° C. for 1 hour. Toluene was removed under vacuum. The desired product was then extracted out using chloroform, washed with brine to obtain 0.48 g of the title compound. The product was further purified by flash column chromatography using ethyl acetate:methanol (10:1) as eluent.

$^1$H NMR (250 MHz Varian; CDCl$_3$): 0.89 δ (3 H, t, J=6.25 Hz); 1.91–2.21 δ (2 H, m); 2.09 δ (3 H, s); 2.69–2.91 δ (2 H, ABq, J$_1$=1.75 Hz; J2=4.25 Hz); 3.41 δ (1 H, dd, J=5.75 Hz); 3.58 δ (1 H, m); 2.55 δ (1 H, dd, J=7.75 Hz); 5.24 δ (1 H; ABq, J$_{1,2}$=14.25 Hz); 6.59–6.72 δ (5 H, d, J=8.5 Hz)

EXAMPLE 40

10-Fluorocamptothecin

10-Fluoro-1-acetyl tetrahydrocamptothecin (0.45 g, 1.1 mmol) in 20 mL 20% sulfuric acid was refluxed for 2 hours. After cooling to room temperature, the reaction mixture was extracted with chloroform, washed with brine and then with a saturated solution of sodium bicarbonate. The product was then dried over anhydrous sodium sulfate. Solvent was removed to deliver 0.26 g 10-fluoro-tetrahydrocamptothecin (64% yield).

To the above 10-fluoro-tetrahydrocamptothecin (0.26 g, 0.7 mmol) in 20 mL of peroxide free 1,4-dioxane and to it was added 0.35 g of DDQ. The mixture was refluxed for 1 hour, then cooled to room temperature. Precipitate was washed with chloroform. The obtained organic portion was combined with mother liquid and washed with a saturated solution of sodium bicarbonate, 2% aqueous HCl, brine, and then dried over anhydrous sodium sulfate. Solvent was evaporated to obtain 0.26 g of 10-fluorocamptothecin in quantitative yield.

$^1$H NMR (250 MHz Varian; CDCl$_3$): 0.89 d (3 H, t, J=6.25 Hz); 1.91–2.21 d (2 H, m); 3.59 d (1 H, s); 5.22 d (2 H, s); 5.24 d (1 H; ABq, J$_{1,2}$=14.25 Hz); 7.53–7.67 d (3 H, m); 8.24 d (1 H, dd, J=4.25 Hz), 8.34 d (1 H,s)

EXAMPLE 41

10-Fluoro-7-(β-trimethylsilyl)ethyl Camptothecin

The 10-fluoro camptothecin intermediate (60 mg) was suspended in water (10 mL) and iron (II) sulfate heptahydrate (100 mg) was added and stirred for approximately 15 minutes. To the above suspension was then added 3-trimethylsilyl propanal (0.5 mL), followed by glacial acetic acid (5 mL) as co-solvent. The colloidal reaction mixture was then stirred and concentrated sulfuric acid (4 mL) added while cooling. Once addition of acid was complete, the pot temperature was raised to room temperature and 30% hydrogen peroxide in water (0.5 mL) added. The reaction mixture was then stirred for 6 hours during which time the reaction was completed. The reaction mixture was then poured into crushed ice and allowed to stand for 2 hours. The precipitated product was then filtered and washed with water followed by hexanes, and dried to deliver the title compound as a pale yellow powder. The crude product was then flash chromatographed over silica gel (mesh 100–230) using chloroform to 5% chloroform-methanol as a gradient. The desired fractions were pooled together, the solvent evaporated, and dried to produce the target compound in 45% yield.

$^1$H NMR (250 MHz Varian; CDCl$_3$): 0.139 d (9 H,s); 0.88 d (2 H, m); 1.02 d (3 H, t, J=6.25 Hz); 1.91–2.21 d (2 H, m); 3.59 d (1 H, s); 5.22 d (2 H, s); 5.24 d (2 H; ABq, J$_{1,2}$=14.25 Hz); 7.57–7.61 d (3 H, m); 8.24 d (1 H, dd, J=4.25 Hz)

$^{13}$C NMR (300 MHz, Varian, CDCl$_3$) δ –2.03, 7.69, 17.43, 24.22, 31.49, 49.17, 66.33, 72.71, 98.19, 107.07, 107.38, 118.71, 120.37, 120.71, 126.87, 133.18, 146.45, 146.78, 150.31, 157.76, 163.10, 174.09.

EXAMPLE 42

9-Nitrocamptothecin

Camptothecin (25 g) in concentrated sulfuric acid (500 mL) was cooled in an ice-bath. To it was then added 70% nitric acid (30 mL), drop-wise to control the reaction temperature. The reaction mixture was then stirred for 36 hours, poured into excess crushed ice and the organic portion was extracted out using chloroform. The combined organic fraction was washed with freshly prepared 10% sodium bicarbonate solution and brine, and then dried over anhydrous sodium sulfate. Solvent was removed and the residue was purified by flash silica gel column using hexane/ethyl acetate (1:1) as eluent to furnish 2.7 g of 9-nitrocamptothecin.

EXAMPLE 43

20-Acetoxy-9-nitro camptothecin

To 9-nitrocamptothecin (1.12g) in glacial acetic acid (10 mL) was added excess acetyl chloride at room temperature. After the mixture was stirred at room temperature for 24 hours, it was poured into ice, extracted with methylene chloride. The methylene chloride solution was washed with brine and dried over sodium sulfate. The solvent was evaporated. The crude product was subsequently purified by flash column chromatography to get 0.88 g of 9-nitro-20-acetoxycamptothecin.

EXAMPLE 44

20-Acetoxy-9-amino camptothecin 9-nitro-20-acetoxycamptothecin (1.5 g) was dissolved in 150 ml reagent grade ethyl acetate. Platinum dioxide (276 mg) was then added to the above solution at room temperature. The mixture was bubbled with hydrogen for approximately 30 minutes and stirred for about an hour. Methanol was then added to dissolve the precipitate. The catalyst was filtered and solvent was removed. The crude product was recrystallized from a mixture of methylene chloride and diethyl ether to give 1.14 g of 9-animo-20-acetoxycamptothecin.

EXAMPLE 45

9-Fluorocamptothecin

Boron trifluoride etheral solution (0.54 mL) in 10 mL anhydrous methylene chloride was taken in a three-neck round bottom flask fitted with an additional funnel and a thermometer. The reaction mixture was then cooled down using ice-acetone bath. To the above solution was then added dropwise at –15° C. 9-amino-20-acetoxy camptothecin (1.14 g, 2.8 mmol) in 100 mL methylene chloride. After an hour, t-butyl nitrite (0.39 mL) in 20 mL methylene chloride was introduced dropwise. The reaction mixture was then stirred in the ice-acetone bath for about 40 minutes. Solvent was removed and to the residue 200 mL of reagent grade toluene was added. The mixture was refluxed under nitrogen for approximately 3 hours. Organic portion was decanted from the residue and concentrated under vacuum. The crude product was purified by flash column chromatography using hexane and ethyl acetate (1:2) as eluent to deliver 380 mg of 9-fluoro-20-acetoxycamptothecin.

To 9-fluoro-20-acetoxycamptothecin (380 mg) in 30 mL methanol was added 107 mg potassium carbonate and two drops of water. After stirring the reaction mixture for about 3 hours, 37% hydrochloric acid was used to adjust pH acidic. The product was precipitated out upon dilution with crushed ice. Mother liquid was concentrated to one-third volume and precipitated the product as mentioned above. The precipitated product was then washed with diethyl ether. The pale yellow product thus obtained is then dried (260 mg) and characterized to 9-fluorocamptothecin.

$^1$H NMR (300 MHz, DMSO- d6): 0.86 δ (t, J=7.2 Hz, 3 H), 1.85 δ (m, 2 H), 5.28 δ (s, 2 H), 5.42 δ (s, 2 H), 6.53 δ (broad, 1 H), 7.35 δ (s, 1 H), 7.54 δ (t, J=8.8 Hz, 1 H), 7.86 δ (q, J=8.5 Hz, 1 H), 8.01 δ (d, J=8.4 Hz, 1 H), 8.82 δ (s, 1 H)

EXAMPLE 46

9-Fluoro-7-(β-trimethylsilyl)ethyl camptothecin

The 9-fluoro camptothecin intermediate (75 mg) was suspended in water (10 mL), added iron (II) sulfate heptahydrate (150 mg) and stirred well for approximately 15 minutes. To the above suspension was then added 3-trimethylsilyl propanal (0.5 mL) followed by glacial acetic acid (5 mL) as co-solvent. The colloidal reaction mixture was then stirred and added concentrated sulfuric acid (4 mL) while cooling. Once addition of acid was over, the pot temperature was raised to room temperature and 30% hydrogen peroxide in water (0.5 ml) added. The reaction mixture was then allowed to stir for 6 hours at which time the reaction was over. The reaction mixture was then poured into crushed ice and allowed to stand for 2 hours. The precipitated product was then filtered and washed with water followed by hexanes, and dried to get the title compound in pale yellow powder. The crude product was then flash chromatographed over silica gel (mesh 100–230) using chloroform to 5% chloroform/methanol as a gradient. The desired fractions were pooled together, the solvent evaporated and dried to get the title compound in 45% yield.

$^1$H NMR (250 MHz Varian; CDCl$_3$): 0.154 δ (9 H,s); 0.94 δ (2 H, m); 1.04 δ (3 H, t, J=6.25 Hz); 1.91–2.21 δ (2 H, m); 3.19 δ (2 H, m) 3.59 δ (1 H, s); 5.22 δ (2 H, s) ; 5.24 δ (2 H; ABq, J$_{1,2}$=14.25 Hz); 7.57–7.71 δ (3 H, m); 8.08 δ (1 H, dd, J=4.25 Hz)

$^{13}$C NMR: δ −2.08, 7.68, 13.99, 18.25, 22.54, 27.28, 27.43, 31.5, 49.28, 66.31, 72.7, 98.4, 112.72, 113.03, 117.62, 118.99, 126.89, 127.47, 129.54, 129.67, 146.73, 147.14, 150.23, 151.41, 152.67, 157.72, 161.1, 174.03

The foregoing description has been directed to particular embodiments of the invention in accordance with requirements of the Patent Statutes for the purposes of illustration and explanation. It will be apparent, however, to those skilled in this art, that many modifications, changes and variations in the claimed antitumor compositions, solutions, methods of administration of the antitumor compositions set forth will be possible without departing from the scope and spirit of the claimed invention. It is intended that the following claims be interpreted to embrace all such modifications and changes.

What is claimed is:

1. A compound having the formula:

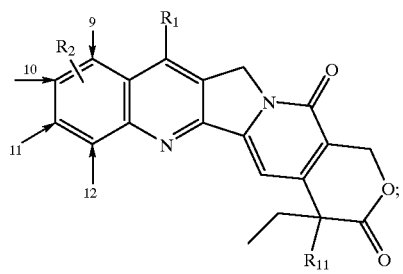

(I)

wherein:

$R_1$ is formyl; acetyl; propionyl; butyryl; $C_2$–$C_8$ alkenyl, or $C_2$–$C_8$ alkynyl, optionally substituted by one or more halogen atoms or $OR_4$ or lower alkyl for a corresponding hydrogen atom therein; arylalkenyl; arylalkynyl; heterocyclyl; —S(O)— lower alkyl; -lower alkyl-P(O)$R_6R_7$, or X-($C_0$–$C_6$ alkylene, lower alkenylene, or lower alkynylene)-SiR$_8$R$_9$R$_{10}$;

$R_2$ is halo, lower alkyl, amino or nitro;

$R_4$ is hydrogen or lower alkyl;

$R_5$ is hydrogen or lower alkyl;

$R_6$ and $R_7$ are each individually hydrogen or lower alkyl;

$R_8$, $R_9$ and $R_{10}$ are each individually hydrogen or lower alkyl;

$R_{11}$ is hydrogen, hydroxy, or acetoxy; and

X is sulfur or X is absent; or a pharmaceutically acceptable salt thereof.

2. The compound of claim 1 wherein $R_1$ is —X-($C_0$–$C_6$ alkylene, alkenylene, or alkynylene)-SiR$_8$R$_9$R$_{10}$, and $R_2$ is halo.

3. The compound of claim 1 or claim 2 wherein $R_2$ is attached to the bonded to the scaffold at the 10-position.

4. The compound of claim 1 or claim 2 wherein $R_2$ is attached to the bonded to the scaffold at the 11-position.

5. The compound of claim 1 or claim 2 wherein $R_2$ is attached to the bonded to the scaffold at the 12-position.

6. The compound of claim 1 or claim 2 wherein $R_2$ is attached to the bonded to the scaffold at the 9-position.

7. The compound of claim 1 wherein said compound is 10-fluoro-7-(β-trimethylsilyl)ethyl camptothecin.

8. The compound of claim 1 wherein said compound is 9-fluoro-7-(β-trimethylsilyl)ethenyl camptothecin.

9. A method of treating a mammalian patient diagnosed with a camptothecin susceptible tumor or a camptothecin susceptible leukemia, said method comprising administering an effective amount of one of the formula I compounds according to claim 1 to said mammalian patient.

10. A pharmaceutical formulation consisting essentially of an effective amount of a formula I compound according to claim 1 and one or more pharmaceutically acceptable diluents or excipients.

* * * * *